United States Patent
Bergmann et al.

(10) Patent No.: US 7,276,592 B2
(45) Date of Patent: Oct. 2, 2007

(54) NUCLEOTIDE ANALOGS WITH SIX-MEMBERED RINGS

(75) Inventors: Frank Bergmann, Iffeldorf (DE); Horst Donner, Munich (DE); Herbert Von Der Eltz, Weilheim (DE); Dieter Heindl, Paehl (DE); Piet Herdewijn, Wezemaal (BE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 490 days.

(21) Appl. No.: 10/816,298

(22) Filed: Apr. 1, 2004

(65) Prior Publication Data
US 2005/0004078 A1 Jan. 6, 2005

(30) Foreign Application Priority Data
Apr. 5, 2003 (EP) .................................. 03007844

(51) Int. Cl.
*C07G 3/00* (2006.01)
*C07H 21/00* (2006.01)
*C07H 19/04* (2006.01)
*C12Q 1/68* (2006.01)

(52) U.S. Cl. ...................... 536/4.1; 536/23.1; 536/25.3; 536/26.6

(58) Field of Classification Search ................ 536/23.1, 536/25.3, 26.6, 4.1; 435/6
See application file for complete search history.

(56) References Cited

U.S. PATENT DOCUMENTS

| 4,458,066 A | 7/1984 | Caruthers et al. |
|---|---|---|
| 4,996,143 A | 2/1991 | Heller et al. |
| 5,002,867 A | 3/1991 | Macevicz |
| 5,130,238 A | 7/1992 | Malek et al. |
| 5,130,446 A | 7/1992 | Musso et al. |
| 5,143,854 A | 9/1992 | Pirrung et al. |
| 5,202,231 A | 4/1993 | Drmanac et al. |
| 5,210,015 A | 5/1993 | Gelfand et al. |
| 5,314,893 A | 5/1994 | Tino et al. |
| 5,451,463 A | 9/1995 | Nelson et al. |
| 5,487,972 A | 1/1996 | Gelfand et al. |
| 5,516,785 A | 5/1996 | Zoltewicz et al. |
| 5,545,522 A | 8/1996 | Van Gelder et al. |

(Continued)

FOREIGN PATENT DOCUMENTS

DE 39 43 522 A1 2/1991

(Continued)

OTHER PUBLICATIONS

Abramson, R.D., Myers, T.W., "Nucleic Acid Amplification Technologies", Current Opinion in Biotechnology 1993, 4:41-47.

(Continued)

*Primary Examiner*—Jezia Riley
(74) *Attorney, Agent, or Firm*—Marilyn L. Amick

(57) ABSTRACT

The present invention is related to compounds comprising six-membered rings capable of being incorporated into nucleic acids. Particularly, the six-membered ring is a derivative of cyclohexane, cyclohexene, tetrahydropyran, tetrahydrothiopyran or piperidine. These compounds may be used to build up oligomeric compounds. The invention is further related to uses of these oligomeric compounds for hybridization and as probes. In addition, methods for the detection of nucleic acids are provided wherein the oligomeric compounds are used.

17 Claims, 9 Drawing Sheets

U.S. PATENT DOCUMENTS

| | | | |
|---|---|---|---|
| 5,565,322 | A | 10/1996 | Heller |
| 5,607,922 | A | 3/1997 | DeClercq et al. |
| 5,668,113 | A | 9/1997 | DeClercq et al. |
| 5,804,375 | A | 9/1998 | Gelfand et al. |
| 5,849,489 | A | 12/1998 | Heller |
| 5,891,636 | A | 4/1999 | Van Gelder et al. |
| 6,022,963 | A | 2/2000 | McGall et al. |
| 6,103,476 | A | 8/2000 | Tyagi et al. |
| 6,130,323 | A | 10/2000 | Su et al. |
| 6,156,501 | A | 12/2000 | McGall et al. |
| 6,162,603 | A | 12/2000 | Heller |
| 6,174,670 | B1 | 1/2001 | Wittwer et al. |
| 6,291,170 | B1 | 9/2001 | Van Gelder et al. |
| 6,344,316 | B1 | 2/2002 | Lockhart et al. |
| 6,613,894 | B1 * | 9/2003 | Miculka et al. .......... 536/25.33 |
| 2002/0165372 | A1 | 11/2002 | McGall et al. |
| 2002/0165389 | A1 | 11/2002 | Vinayak et al. |

FOREIGN PATENT DOCUMENTS

| | | |
|---|---|---|
| EP | 0 439 182 B1 | 7/1991 |
| EP | 0 468 352 A2 | 1/1992 |
| EP | 0 476 014 B1 | 3/1992 |
| EP | 0 646 125 B1 | 4/1995 |
| EP | 0 313 219 B1 | 5/1996 |
| EP | 1 251 168 A1 | 10/2002 |
| EP | 1 251 179 A2 | 10/2002 |
| EP | 1 254 962 A1 | 11/2002 |
| EP | 0 135 587 B2 | 12/2002 |
| WO | WO89/10977 | 11/1989 |
| WO | WO89/11548 | 11/1989 |
| WO | WO90/01069 | 2/1990 |
| WO | WO90/15070 | 12/1990 |
| WO | WO91/15488 | 10/1991 |
| WO | WO92/00989 | 1/1992 |
| WO | WO92/02638 | 2/1992 |
| WO | WO92/08808 | 5/1992 |
| WO | WO92/10092 | 6/1992 |
| WO | WO93/17020 | 9/1993 |
| WO | WO93/17126 | 9/1993 |
| WO | WO93/25565 | 12/1993 |
| WO | WO96/05213 | 2/1996 |
| WO | WO96/41811 | 12/1996 |
| WO | WO97/27317 | 7/1997 |
| WO | WO97/30064 | 8/1997 |
| WO | WO97/43451 | 11/1997 |
| WO | WO98/25943 | 6/1998 |
| WO | WO99/15509 | 4/1999 |
| WO | WO 00/06771 | 2/2000 |
| WO | WO 00/58493 | 10/2000 |
| WO | WO 01/02417 A1 | 1/2001 |
| WO | WO 01/18003 A1 | 3/2001 |
| WO | WO 01/37291 A1 | 5/2001 |
| WO | WO 01/49687 | 7/2001 |
| WO | WO 01/85220 | 11/2001 |
| WO | WO 02/12263 A1 | 2/2002 |
| WO | WO 02/18406 | 3/2002 |
| WO | WO 02/072779 | 9/2002 |

OTHER PUBLICATIONS

Allart, B., Busson, R., Rozenski, J., Van Aerschot, A., Herdewijn, P., "Syntehsis of Protected D-Altritol Nucleosides as Building Blocks For Oligonucleotide Synthesis", Tetrahedron 55 (1999) 6527-6546.

Allart, B., Khan, K., Rosemeyer, H., Schepers, G., Hendrix, C., Rothenbacher, K., Seela, F., VanAerschot, A., Herdewijn, "D-Altritol Nucleic Acids (ANA): Hybridisation Properties, Stability, and Initial Structural Analysis", Chem. Eur. J., 1999, 5, No. 8, pp. 2424-2431.

Andersen, M.W., Dalage, S.M., Kerremans, L., Herdewijn, P., "The Synthesis of Modified D- and L- Anhydrohexitol Nucleosides", Abstract: 1996.

Arango, J.H., Geer, A., Rodriguez, J., Young, P.E., Scheiner, P., "Cyclohexenyl Nucleosides and Related Compounds", Nucleosides & Nucleotides, 12(7), 773-784 (1993).

Atkins, D., Miller, M., DeBouvere, B., VanAerschot, A., Herdewijn, P., "Evaluation of the cellular uptake of hexitol nucleic acids in HeLa cells", Pharmacology 55, (2000), pp. 615-617.

Barany, F., "Genetic Disease Detection and DNA Amplification Using Cloned Thermostable Ligase", Proc. Natl. Acad. Sci. USA, vol. 88, Jan. 1991, pp. 189-193.

Barany, F., "The Ligase Chain Reaction in a PCR World", PCR Methods and Applications, 1:5-16, 1991.

Beaucage, S.L., Caruthers, M.H., "Deoxynucleoside Phosphoramidites—A New Class of Key Intermediates for Deoxypolynucleotide Synthesis", Tetrahedron Letters, vol. 22, No. 20, pp. 1859-1862, 1981.

Boudou, V., Kerremans, L., DeBouvere, B., Lescrinier, E., Schepers, G., Busson, R., VanAerschot, A., Herdewijn, P. "Base pairing of anhydrohexitol nucleosides with 2,6-diaminopurine, 5-methycytosine and uracil as base moiety", Nucleic Acids Research, 1999, vol. 27, No. 6, pp. 1450-1456.

Brown, E.L., Belagaje, R., Ryan, M.J., Knorana, H.G. "Chemical Synthesis and Cloning of a Tyrosine tRNA Gene", Methods in Enzymology, vol. 68, 1979, pp. 109-151.

Brown, S.G., King, B.F., Kim, Y.C., Jang, S.Y., Burnstock, G., Jacobson, K.A., "Activity of Novel Adenine Nucleotide Derivatives as Agonists and Antagonists at Recombinant Rat P2X Receptors", Drug Development Research, 49:253-259 (2000).

DeBouvere, B., Kerremans, L., Rozenski, J., Janssen, G., Aerschot, A.V., Claes, P., Busson, R., Herdewijn, P. "Improved Synthesis of Anhydrohexitol Building Blocks for Oligonucleotide Synthesis", Liebigs Ann./Recueil, 1997, 1453-1461.

DeWinter, H., Lescrinier, E., Van Aerschot, A., Herdewijn, P. "Molecular Dynamics Simulation to Investigate Differences in Minor Groove Hydration of HNA/RNA Hybrids As Compared to HNA/DNA Complexes", J. Am. Chem. Soc., 1998, 120, 5381-5394.

Froeyen, M., Wroblowski, B., Esnoufl R., DeWinter, H., Allart, B., Lescrinier, E., Herdewija, P. "Molecular-Dynamics Studies of Single-Stranded Hexitol, Altritol, Mannitol, and Ribose Nucleic Acids (HNA, MNA, ANA, and RNA, Resp.) and of the Stability of HNA-RNA, ANA-RNA, and MNA-RNA Duplexes", Helvetica Chimica Acta, vol. 83, (2000), 2153-2182.

Garegg, P.J., Regberg, T., Stawinski, J., Stromberg, R., "Formation of Internucleotidic Bonds via Phosphonate Intermediates", Chemica Scripta 1985, 25, 280-282.

Giegrich, H., Eisele-Buhler, S., Hermann, C., Kvasyuk, E., Charubala, R., Pfeiderer, W., "New Photolabile Protecting Groups in Nucleoside and Nucleotide Chemistry—Synthesis, Cleavage Mechanisms and Applications", Nucleosides & Nucleotides, 17(9-11), 1987-1996 (1998).

Guatelli, J.C., Whitfield, K.M., Kwoh, D.Y., Barringer, K.J., Richman, D.D., Gingeras, T.R., "Isothermal, in vitro amplification of nucleic acids by a multienzyme reaction modeled after retroviral replication", Proc. Natl. Acad. Sci. USA, vol. 87, pp. 1874-1878, Mar. 1990.

Hendrix, C., Rosemeyer, H., Verheggen, I., Seela, F., Van Aerschot, A., Herdewijn, P., "1'5'-Anhydrohexitol Oligonucleotides: Synthesis, Base Pairing and Recognition by Regular Oligodeoxyribonucleotides and Oligoribonucleotides", Chem. Eur. J., 1997, 3, No. 1, pp. 110-120.

Hendrix, C., Rosemeyer, H., Verheggen, I., Seela, F., Van Aerschot, A., Herdewijn, P., "1'5'-Anhydrohexitol Oligonucleotides: Hybridisation and Strand Displacement with Oligoribonucleotides, Interaction with RNase H and HIV Reverse Transcriptase", Chem. Eur. J., 1997, 3, No. 9, pp. 1513-1520.

Herdewijn, P., Doboszewski, B., Verheggen, I., Van Aerschot, A., "1,3,4-Substituted pyranosyl-like oligonucleotides", Nucleic Acids Symposium Series, No. 31, pp. 161-162, 1994.

Hoheisel, J.D., "Oligomer-chip technology", TIBTECH, Nov. 1997, vol. 15, pp. 465-469.

Hossain, N., Wroblowski, B., Van Aerschot, A., Rozenski, J., DeBruyn, A., Herdewijn, P., "Oligonucleotides Composed of 2'-Deoxy-1',5'-anhydro-d-mannitol Nucleosides with a Purine Base Moiety", J. Org. Chem. 1998, 63, 1574-1582.

Jung, K.E., Kim, K., Yang, M., Lee, K., Lim, H., "Synthesis and Hybridization Properties of Oligonucleotides Containing 6-Membered Azasugar Nucleotides", Bioorganic & Medicinal Chemistry Letters 9, (1999), 3407-3410.

Katagiri, N., Ito, Y., Shiraishi, T., Maruyama, T., Sata, Y., Kaneko, C., "Deamination of 9-(Hydroxymethylated Cycloalkyl)-9H-Adenines (Carbocyclic Adeninonucleosides) by Adenosine Deaminase: Effect of High-Pressure Upon Deamination Rate and Enantioselectivity", Nucleosides & Nucleotides, 15(1-3), 631-647 (1996).

Konkel, M.H., Vince, R., "Synthesis and Biological Activity of Cyclohexenyl Nucleosides, cis-5-(9H-Purin-9-YL)-3-Cyclohexenyl Carbinols and Their 8-Azapurinyl Analogs", Nucleosides & Nucleotides, 14(9&10), 2061-2077 (1995).

Konkel, M.J., Vince, R., "Cyclohexenyl Nucleotides: Synthesis of cis-4-(9H-Purin-9-yl)-2-cyclohexenylcarbinols", Tetrahedron, vol. 52, No. 3, pp. 799-808, 1996.

Kozlov, I.A., DeBouvere, B., Van Aerschot, A., Herdewijn, P., Orgel, L.E., "Efficient Transfer of Information from Hexitol Nucleic Acids to RNA during Nonenzymatic Oligomerization", J. Am. Chem. Soc. 1999, 121, 5856-5859.

Kozlov, I.A., Politis, P.K., Pitsch, S., Herdewijn, P., Orgel, L.E., "A Highly Enantio-Selective Hexitol Nucleic Acid Template for Nonenzymatic Oligoguanylate Synthesis", Journal of the American Chemical Society, vol. 121, No. 5, pp. 1108-1109, 1999.

Kozlov, I.A., Politis, P.K., Van Aerschot, A., Busson, R., Herdewijn, P., Orgel, L.E., "Nonenzymatic Synthesis of RNA and DNA Oligomers on Hexitol Nucleic Acid Templates: The Importance of the A Structure", Journal of the American Chemical Society, vol. 121, No. 12, Mar. 31, 1999, pp. 2653-2656.

Kozlov, I.A., Zielinski, M., Allart, B., Kerremans, L., Van Aerschot, A., Busson, R., Herdewijn, P., Orgel, L.E., "Nonenzymatic Template-Directed Reactions on Altritol Oligomers, Preorganized Analoques of Oligonucleotides", Chem. Eur. J. 2000, 6, No. 1, pp. 151-155.

Kwoh, D.Y., Davis, G.R., Whitfield, K.M., Chappelle, H.L., DiMichele, L.J., Gingeras, T.R., "Transcription-based amplifiaction system and detection of amplified human immunodeficiency virus type 1 with a bead-based sandwich hybridization format", Proc. Natl. Acad. Sci, USA, vol. 86, Feb. 1989, pp. 1173-1177.

Lescrinier, E., Esnouf, R., Schraml, J., Busson, R., Heus, H.A., Hilbers, C.W., Herdewijn, P., "Solution structure of a HNA-RNA hybrid", Chemistry & Biology 2000, 7:719-731.

Lescrinier, E., Esnouf, R.M., Schraml, J., Busson, R., Herdewijn, P., "Solution Structure of a Hexitol Nucleic Acid Duplex with Four Consecutive T—T Base Pairs", Helvetica Chimica Acta, vol. 83, (2000), 1291-1310.

Luyten, I., Herdewijn, P., "Synthesis and Conformational Behavior of Purine and Pyrimidine B-D-threo-Hex-3'-enopyranosyl Nucleosides", Tetrahedron, vol. 52, No. 27, pp. 9249-9262, 1996.

Maurinsh, Y., Rosemeyer, H., Esnouf, R., Medvedovici, A., Wang, J., Ceulemans, G., Lescrinier, E., Hendrix, C., Busson, R., Sandra, P., Seela, F., Van Aeroschot, A., Herdewijn, P., "Synthesis and Pairing Properties of Oligonucleotides Containing 3-Hydroxy-4-hydroxymethyl-1-cyclohexanyl Nucleosides", Chem. Eur. J. 1999, 5, No. 7, pp. 2139-2150.

Maurinsh, Y., Schraml, J., DeWinter, H., Blaton, N., Peeters, O., Lescrinier, E., Rozenski, J., Van Aerschot, A., DeClercq, E., Busson, R., Herdewijn, P., "Synthesis and Conformational Study of 3-Hydroxy-4-(Hydroxymethyl)-1-Cyclohexanyl Purines and Pyrimidines", J. Org. Chem., 1997, 62, 2861-2871.

Narang, S.A., Hsiung, H.M., Brosseau, R., "Improved Phosphotriester Method of the Synthesis of Gene Fragments", Methods in Enzymology, vol. 68, 1979. pp. 90-98.

Ostrowski, T., Wroblowski, B., Busson, R., Rozenski, J., DeClercq, E., Bennett, M.S., Champness, J.N., Summers, W.C., Sanderson, M.R., Herdewijn, P. "5-Substituted Pyrimidines with a 1,5-Anhydro-2,3-dideoxy-d-arabino-hexitol Moiety at N-1: Synthesis, Antiviral Activity, Conformational Analysis, and Interaction with Viral Thymidine Kinase", J. Med. Chem. 1998, 41, 4343-4353.

Perez, M.J., DeClercq, E., Herdewijn, P., "Synthesis and Antiviral Activity of 2-Deoxy-1,5-Anhydro-D-Mannitol Nucleosides Containing a Pyrimidine Base Moiety", Bioorganic & Medicinal Chemistry Letters, vol. 6, No. 13, pp. 1457-1460, 1996.

Perez, M.J., Rozenski, J., Busson, R., Herdewijn, P., "Application of the Mitsunobu-Type Condensation Reaction to the Synthesis of Phosphonate Derivatives of Cyclohexenyl and Cyclohexanyl Nucleosides", J. Org. Chem., 1995, 60, 1531-1537.

Pochet, S., VanAerschot, A., Herdewijn, P., Marliere, P., "Replicative Capability of Anhydrohexitol Analogues of Nucleotides", Nucleosides & Nucleotides, 18 (4&5), 1015-1017 (1999).

Pravdic, N., Zidovec, B., Franjic, I., Fletcher, Jr., H.G., "Catalytic Hydrogenation of Some 2-Acetamindoaldose Derivatives", Croatica Chemica Acta 45 (1973), pp. 343-356.

Ramesh, K., Wolfe, M.S., Lee, Y., VanderVelde, D., Borchardt, R.T., "Synthesis of Hydroxylated Cyclohexenyl- and Cyclohexanyladenines as Potential Inhibitors of S-Adenosylhomocysteine Hydrolase", J. Org. Chem. 1992, 57, 5861-5868.

Rosenquist, A., Kvarnstrom, I., "Synthesis of Enantiomerically Pure Bis (hydroxymethyl)-Branched Cyclohexenyl and Cyclohexyl Purines as Potential Inhibitors of HIV", J. Org. Chem. 1996, 61, 6282-6288.

Su, S.H., Iyer, R.S., Aggarwal, S.K., Kaira, K.L., "Novel Non-Nucleosidic Phosphoramidites for Oligonucleotide Modification and Labeling", Biorganic & Medicinal Chemistry Letters, vol. 7, No. 13, pp. 1639-1644, 1997.

Torimura, M., Kurata, S., Yamada, K., Yokomaku, T., Kamagata, Y., Kanagawa, T., Kurane, R., "Fluorescence-Quenching Phenomenon by Photoinduced Electron Transfer between a Fluorescent Dye and a Nucleotide Base", Analytical Sciences, Jan. 2001, vol. 17, 2001, 155-160.

Uhlmann, E., Peyman, A., "Antisense Oligonucleotides: A New Therapeutic Principle", Chemical Reviews, vol. 90, No. 4, Jun. 1990, pp. 544-584.

VanAerschot, A., Verheggen, I., Herdewijn, P., "Synthesis of nucleoside analogues with a 1,5-anhydrohexitol moiety", Bioorganic & Medical Chemistry Letters, vol. 3, No. 6, pp. 1013-1018, 1993.

Vandermeeren, M., Preveral, S., Janssens, S., Geysen, J., Saison-Behmoaras, E., VanAerschot, A., Herdewijn, P. "Biological Activity of Hexitol Nucleic Acids Targeted at Ha-ras and Intracellular Adhesion Molecule-1 mRNA", Biochemical Pharmacology, vol. 59, pp. 655-663, 2000.

Vastmans, K., Kerremans, L., Hendrix, C., VanAerschot, A., Pochet, S., Marliere, P., Herdewijn, P. "Recognition of 1,5-Anhydrohexitol Adenine Triphosphate by a DNA Polymerease", Collection Symposium Series, vol. 2, 1999, pp. 156-160.

Vastmans, K., Pochet, S., Peys, A., Kerremans, L., VanAerschot, A., Hendrix, C., Marliere, P., Herdewijn, P. "Enzymatic Incorporation in DNA of 1,5-Anhydrohexitol Nucleotides", Biochemistry, vol. 39, No. 42, pp. 12757-12765, 2000.

Vastmans, K., Rozenski, J., VanAerschot, A., Herdewijn, P. "Recognition of HNA and 1,5-anhydrohexitol nucleotides by DNA metabolizing enzymes", Biochimica et Biophysica Acta 1597 (2002) 115-122.

Verheggen, I., VanAerschot, A., Rozenski, J., Janssen, G., DeClercq, E., Herdewijn, P., "Synthesis of 1,5-Anhydrohexitol Nucleosides as Mimics of ATZ, D4T and DDC+", Nucleosides & Nucleotides, 15(103), 325-335 (1996).

Verheggen, I., VanAerschot, A., Toppet, S., Snoeck, R., Janssen, G., Balzarini, J., DeClercq, E., Herdewijn, P. "Synthesis and Antiherpes Virus Activity of 1,5-Anhydrohexitol Nucleosides", Journal of Medicinal Chemistry, 1993, 36, pp. 2033-2040.

Verma, S., Eckstein, F., "Modified Oligonucleotides: Synthesis and Strategy for Users", Annu. Rev. Biochem. 1998, 67:99-134.

Wang, J., Froeyen, M., Hendrix, C., Andrei, G., Snoeck, R., DeClercq, E., Herdewijn, P. "The Cyclohexene Ring System as a Furanose Mimic: Synthesis and Antiviral Activity of Both Enantiomers of Cyclohexenylguanine". J. Med. Chem 2000, 43; 736-745.

Wang, J., Herdewijn, P., "Enantioselective Synthesis and Conformational Study of Cyclohexene Carbocyclic Nucleosides". J. Org. Chem. 1999, 64, 7820-7827.

Wang, J., Verbeure, B., Luyten, I., Froeyen, M., Hendrix, C., Rosemeyer, H., Seela, F., VanAerschot, A., Herdewijn, P., "Cyclohexene Nucleic Acids (CeNA) Form Stable Duplexes With RNA and Induce RNase H Activity", Nucleosides, Nucleotides & Nucleic Acids, 204(4-7), 785-788 (2001).

Wang, J., Verbeure, B., Luyten, I., Leschinier, E., Froeyen, M., Hendrix, C., Rosemeyer, H., Seela, F., VanAerschot, A., Herdewijn, P., "Cyclohexene Nucleic Acids (CeNA): Serum Stable Oligonucleotides that Activate RNase H and Increase Duplex Stability with Complementary RNA", J. Am. Chem. Soc. 2000, 122, 8595-8602.

Whelen, A.C., Persing, D.H., "The Role of Nucleic Acid Amplification and Detection in The Clinical Microbiology Laboratory", Annu. Rev. Microbiol. 1996, 50: 349-373.

Wu, D.Y., Wallace, R.B., "The Ligation Amplification Reaction (LAR)—Amplification of Specific DNA Sequences Using Sequential Rounds of Template-Dependent Ligation", Genomics 4, 560-569 (1989).

* cited by examiner

Fig. 4

| Type of analog | HO—O—base  HO R | | HO—base  HO R | |
|---|---|---|---|---|
| base | A | U | A | |
| R= H | Biotin h-ATP | Biotin h-UTP | Biotin dCe-ATP | |
| R= OH | | Biotin a-UTP | | |

1:5/25/125/625/3125/15625/78125

1:5/25/125/625/3125/15625/78125

1:5/25/625/3125/15625/78125/390625/1953125

1) SP6/Bio-16-UTP

2) SP6/Bio-16-UTP

3) SP6/Bio-aUTP

4) SP6/Bio-aUTP

5) T7/Bio-16-UTP

6) T7/Bio-16-UTP

7) T7/Bio-aUTP

8) T7/Bio-aUTP

9) T3/Bio-16-UTP

10) T3/Bio-16-UTP

11) T7/Bio-aUTP

12) T7/Bio-aUTP

NUCLEOTIDE ANALOGS WITH SIX-MEMBERED RINGS

FIELD OF THE INVENTION

The present invention is related to compounds comprising six-membered rings capable of being incorporated into nucleic acids. Particularly, the six-membered ring is a derivative of cyclohexane, cyclohexene, tetrahydropyran, tetrahydrothiopyran or piperidine. These compounds may be used to build up oligomeric compounds. The invention is further related to uses of these oligomeric compounds for hybridization and as probes. In addition, methods for the detection of nucleic acids are provided wherein the oligomeric compounds are used.

BACKGROUND OF THE INVENTION

In the field of molecular diagnostics, the detection of target nucleic acids with the polymerase chain reaction (PCR) plays an important role. The routine screening of blood banks for the presence of Human Immunodeficiency Virus (HIV), Hepatitis-B (HBV) or C Virus (HCV) is an example for the large-scale application of PCR-based diagnostics. Automated systems for PCR-based analysis often make use of real-time detection of product amplification during the PCR process. Key to such methods is the use of modified oligonucleotides carrying reporter groups or labels.

In its simplest form, PCR is an in vitro method for the enzymatic synthesis of specific nucleic acid sequences, using two oligonucleotide primers that hybridize to opposite strands and flank the target sequence that is the region of interest in the target nucleic acid. A repetitive series of reaction steps involving template denaturation, primer annealing, and the extension of the annealed primers by DNA polymerase (DNA: deoxyribonucleic acid) results in the exponential accumulation of a specific fragment whose termini are defined by the 5' ends of the primers.

The detection of DNA amplification products generated by a PCR process can, on the one hand, be accomplished in separate working steps. These may involve the characterization of amplified fragments with respect to their electrophoretic mobility and/or the analysis of denatured amplification products attached to a solid support using a hybridization probe.

On the other hand, the detection of DNA amplification products can be done in a so-called "homogeneous" assay system. A "homogeneous" assay system comprises reporter molecules or labels which generate a signal while the target sequence is amplified. An example for a "homogeneous" assay system is the TaqMan® system that has been detailed in U.S. Pat. Nos. 5,210,015, 5,804,375 and 5,487,972. Briefly, the method is based on a double-labeled probe and the 5'-3' exonuclease activity of Taq DNA polymerase. The probe is complementary to the target sequence to be amplified by the PCR process and is located between the two PCR primers during each polymerization cycle step. The probe has two fluorescent labels attached to it. One is a reporter dye, such as 6-carboxyfluorescein (FAM), which has its emission spectra quenched by energy transfer due to the spatial proximity of a second fluorescent dye, 6-carboxy-tetramethyl-rhodamine (TAMRA). In the course of each amplification cycle, the Taq DNA polymerase in the process of elongating a primed DNA strand displaces and degrades the annealed probe, the latter due to the intrinsic 5'-3' exonuclease activity of the polymerase. The mechanism also frees the reporter dye from the quenching activity of TAMRA. As a consequence, the fluorescent activity increases with an increase in cleavage of the probe, which is proportional to the amount of PCR product formed. Accordingly, amplified target sequence is measured detecting the intensity of released fluorescence label.

A similar principle of energy transfer between fluorescent dye molecules applies to "homogeneous" assays using so-called "molecular beacons" (U.S. Pat. No. 6,103,476). These are hairpin-shaped nucleic acid molecules with an internally quenched fluorophore whose fluorescence is restored when they bind to a target nucleic acid (U.S. Pat. No. 6,103,476). They are designed in such a way that the loop portion of the molecule is a probe sequence complementary to a region within the target sequence of the PCR process. The stem is formed by the annealing of complementary arm sequences on the ends of the probe sequence. A fluorescent moiety is attached to the end of one arm and a quenching moiety is attached to the end of the other arm. The stem keeps these two moieties in close proximity to each other, causing the fluorescence of the fluorophore to be quenched by energy transfer. Since the quencher moiety is a non-fluorescent chromophore and emits the energy that it receives from the fluorophore as heat, the probe is unable to fluoresce. When the probe encounters a target molecule, it forms a hybrid that is longer and more stable than the stem hybrid and its rigidity and length preclude the simultaneous existence of the stem hybrid. Thus, the molecular beacon undergoes a spontaneous conformational reorganization that forces the stem apart, and causes the fluorophore and the quencher to move away from each other, leading to the restoration of fluorescence which can be detected.

More examples for "homogeneous" assay systems are provided by the formats used in the LightCycler® instrument (see e.g. U.S. Pat. No. 6,174,670), some of them sometimes called "kissing probe" formats. Again, the principle is based on two interacting dyes which, however, are characterized in that the donor-dye excites an acceptor-dye by fluorescence resonance energy transfer. An exemplified method uses two modified oligonucleotides as hybridization probes, which hybridize to adjacent internal sequences of the target sequence of the PCR process. The 5'-located modified oligonucleotide has a donor-dye as a label at its 3' end. The 3'-located modified oligonucleotide has an acceptor-dye at its 5' end. Following the head-to-tail-oriented annealing of the two modified oligonucleotides to the target sequence in the course of an amplification cycle, donor and acceptor dye are brought in close proximity. Upon specific excitation of the donor dye by means of a monochromatic light pulse, acceptor dye fluorescence is detected providing a measure for the amount of PCR product formed.

Another assay format is the so-called "array" format. An "array" is an arrangement of addressable locations on a device (see e.g. U.S. Pat. Nos. 5,143,854, 6,022,963, 6,156,501, WO 90/15070, WO 92/10092). The number of locations can range from several to at least hundreds of thousands. Most importantly, each location represents a totally independent reaction site. Each location carries a nucleic acid as e.g. an "oligomeric compound", which can serve as a binding partner for a second nucleic acid, in particular a target nucleic acid. Methods for the manufacturing thereof are described in EP-A-0 476 014 and Hoheisel, J. D., TIBTECH (1997), Vol. 15,465-469, WO 89/10977, WO 89/11548, U.S. Pat. Nos. 5,202,231, 5,002,867, WO 93/17126). Further development has provided methods for making very large arrays of oligonucleotide probes in very small areas.(U.S. Pat. No. 5,143,854, WO 90/15070, WO 92/10092). Microfabricated arrays of large numbers of oligonucleotide probes, called "DNA chips" offer great promise for a wide variety of applications (see e.g. U.S. Pat. Nos. 6,156,501 and 6,022,963). The basic steps of the method are that nucleic acid from control and treatment samples is isolated and labeled with different fluorescent dyes incorporated during an amplification process. In more detail, this is performed according to the method described in U.S. Pat. Nos. 5,545,522; 5,716,785; 5,891,636; 6,291,170 whereby double stranded cDNA is synthesized with a primer comprising the bacterial T7-Promoter and labeled RNA is transcribed in the presence of ribonucleoside triphosphates whereby labels are attached to some of the nucleoside triphosphates. These labeled nucleic acids are then optionally fragmented, mixed and hybridized to the arrayed oligomeric compounds. An optical device is then used to measure the relative intensities of each dye for each individual spot. The ratio of fluorescence levels between the two probes indicates the relative gene expression between the samples. By these processes researchers can evaluate an entire set of genes simultaneously rather than looking at the effects of single genes one at a time. High differential expression of specific genes can then be followed up by conventional means such as northern blot or quantitative RT-PCR. Data from multiple experiments can be combined in order to assign functional information to genes of otherwise unknown function. Genes showing similar expression profiles across differing states are likely to participate in common physiological or metabolic pathways. Cluster analysis programs have been developed which allow detection of co-expressed groups of genes reflecting information on function.

The oligomeric compound or modified oligonucleotide used in "homogeneous" assay systems comprises nucleotides, modified nucleotides or non-nucleotide compounds, i.e. the monomeric units, to which labels such as dyes as reporter molecules are attached. The features of such monomeric units are that they can be attached to and/or integrated into the sugar-phosphate polymer backbone of a nucleic acid, they do not prevent the pairing of the modified oligonucleotide with its complementary target sequence, and they provide functional groups for the attachment of one or more labels.

These requirements can be fulfilled by nucleotides, modified nucleotides or non-nucleotide compounds. In addition, the TaqMan® format requires that the oligomeric compound can be digested by 5'-3' exonuclease activity of a template-dependent DNA-polymerase. Various modified nucleotides have also been incorporated into oligomeric compounds to influence their hybridization behavior or stability, see e.g. WO02/12263.

Several compounds and their use for incorporation as monomeric units into nucleic acids are known in the art. Such compounds provide functional groups and/or linking moieties for the covalent attachment of reporter groups or labels. In the course of the chemical synthesis of the oligomeric compound, the skeletal structure of the "non-nucleotide compound" or "modified nucleotide" is connected with the "oligonucleotide" backbone, for example by phosphoramidite-based chemistry resulting in a phosphodiester. A given incorporated compound thus represents a "modified nucleotide" or "non-nucleotide compound" within the newly generated "modified oligonucleotide". A label is bound by a reactive group of a linking moiety, exemplified by but not limited to an amino function that is present on the skeletal structure or on the "linking moiety", which connects the skeleton with the reactive group. A label can be covalently attached to the compound prior to the synthesis of a "modified oligonucleotide" or afterwards, upon the removal of an optional protecting group from the functional group to which the label is to be coupled. Various "modified nucleotides" have also been incorporated into oligomeric compounds to influence their hybridization behavior or stability, see e.g. WO02/12263.

Several references disclose modified nucleotides comprising six-membered rings and their incorporation into oligonucleotides. WO 93/25565 discloses 1,5 anhydrohexitol nucleoside analogs and pharmaceutical uses thereof. Further 1,5 anhydrohexitol or hexitol nucleoside analogues are disclosed in Verheggen, I., et al., Nucleosides & Nucleotides 15 (1996) 325-335; Verheggen, I., et al., J. of Med. Chem. 36 (1993) 2033-2040; Pérez-Pérez, M.-J., et al., Bioorg. & Med. Chem. Letters 6 (1996) 1457-1460; Vastmans, K., et al., Collect. Symp. Series 2 (1999) 156-160; Andersen, M. W., et al., Pergamon, Tetrahedron Lett. 37 (1996) 8147-8150; Ostrowski, T., et al., J. Med. Chem. 41 (1998) 4343-4353; Allart, B., et al., Tetrahedron 55 (1999) 6527-6546; De Bouvere, B., et al., Liebigs Ann./Recueil (1997) 1453-1461; Verheggen, I., J. Med. Chem. 38 (1995) 826-835. Antiviral tetrahydropyrans are disclosed in U.S. Pat. No. 5,314,893. A deoxyadenosine bisphosphate derivative containing a six-membered ring is described by Brown, S. G., et al., Drug Development Research 49 (2000) 253-259.

WO 01/18003 describes six-membered at least partially unsaturated carbocyclic nucleoside compounds. Pharmaceutical uses are primarily considered. Further cyclohexane or cyclohexene containing nucleoside analogs are disclosed in Wang, J., et al., J. Med. Chem. 43 (2000) 736-745; Rosenquist, A., et al., J. Org. Chem. 61 (1996) 6282-6288; Ramesh, K., et al., J. Org. Chem. 57 (1992) 5861-5868; Pérez-Pérez, M. J., et al., J. Org. Chem. 60 (1995) 1531-1537; Konkel, M. J., and Vince, R., Tetrahedron 52 (1996) 799-808; Arango, J. H., Nucleosides & Nucleotides 12 (1993) 773-784; Konkel, M. J., and Vince, R., Nucleosides & Nucleotides 14 (1995) 2061-2077; Katagiri, N., et al., Nucleosides & Nucleotides 15 (1996) 631-647; Luyten, I., and Herdewijn, P., Tetrahedron 52 (1996) 9249-9262; Wang, J., et al., J. Med. Chem. 43 (2000) 736-745; Wang, J., and Herdewijn, P., J. Org. Chem. 64 (1999) 7820-7827; Maurinsh, Y., et al., J. Org. Chem. 62 (1997) 2861-2871; Wang, J., et al. Nucleosides Nucleotides Nucleic Acids 20 (2001) 785-788; Maurinsh, Y, et al., Chem. Eur. J. 5 (1999) 2139-2150.

WO 96/05213 discloses oligomers consisting or comprising 1,5 anhydrohexitol nucleoside analogues and their uses. WO97/30064 relates to oligomers comprising or containing 1,5-anhydrohexitol nucleotide analogs which exhibit sequence specific binding to complementary sequences. Further, the synthesis thereof is disclosed and their use in diagnosis, hybridization, isolation of nucleic acids, site-specific DNA modification and therapeutics. Further hexitol or 1,5 anhydrohexitol containing nucleic acids are disclosed in Vastmans, K., et al., Biochem. 39 (2000) 12757-12765; Pochet, S., et al., Nucleosides & Nucleotides 18 (1999) 1015-1017; Kozlov, I. A., et al., Chemistry 6 (2000) 151-155; Vandermeeren, M., et al., Biochem. Pharm. 59 (2000) 655-663; Hendrix, C., et al., Chem. Eur. J. 3 (1997) 1513-1520; Allart, B., et al., Chem. Eur. J. 8 (1999) 2424-2431; Kozlov, I. A., et al., J. Am. Chem. Soc. 121 (1999) 2653-2656; Hendrix, C., et al., Chem. Eur. J. 3 (1997) 110-120; Van Aerschot, A., et al., Angew. Chem. Int. Ed. Engl. 34 (1995) 1338-1339; Froeyen, M., et al., Helvetica Chimica Acta 83 (2000) 2153-2182; Boudou, V., et al., Nucleic Acids Research 27 (1999) 1450-1456; Lescrinier, E., et al., Chem. Biol. 7 (2000) 719-731; Kozlov, I. A., et al., J. Am. Chem.

Soc. 121 (1999) 1108-1109; Herdewijn, P., et al., Nucl. Acids Symp. Series 31 (1994) 161-162; Lescrinier, E., et al., Helvetica Chimica Acta 83 (2000) 1291-1310; Kozlov, I. A., et al., J. Am. Chem. Soc. 121 (1999) 5856-5859; De Winter, H., et al., J. Am. Chem. Soc. 120 (1998) 5381-5394; Atkins, D., et al., Pharmazie 55 (2000) 615-617. Pyranosyl oligomers are also disclosed in WO 98/25943 and WO 99/15509.

WO 01/49687 discloses cyclohexene nucleic acids, their hybridization behavior to RNA and the use in diagnostics and therapy. Further cyclohexane or cyclohexene containing nucleic acids are disclosed in Wang, J., et al., J. Am. Chem. Soc. 122 (2000) 8595-8602; Maurinsh, Y., et al., Chem. Eur. J. 5 (1999) 2139-2150.

WO97/27317 and WO 02/072779 disclose various compounds for nucleic acid labeling.

EP 0468352 discloses nucleic acid derivatives comprising a general formula that contains a six-membered ring but which contain an additional methylene group at the C4 atom of the six-membered ring. WO01/02417 and Jung, K.-E., Bioorg. Med. Chem. Lett. 9 (1999) 3407-3410 disclose a nucleotide monomer containing a six-membered aza-sugar and oligomers containing them.

Compounds to be used for the incorporation of labels into nucleic acids or to influence the properties of the modified oligonucleotide have to be carefully selected as they may interfere with base pairing, fail to provide a skeletal structure of sufficient rigidity, provide largely hydrophobic structures resulting in low water solubility, provide only limited amenability to chemical modifications, or comprise mixtures of enantiomers. Therefore, it was an object of the present invention to provide new compounds to be used for the incorporation of labels into nucleic acids or to influence their properties.

SUMMARY OF THE INVENTION

The present invention is related to compounds comprising six-membered moieties, in particular specific compounds comprising hexitol or cyclohexene moieties which may be used to build up oligomeric compounds. The invention is further related to uses of these oligomeric compounds for hybridization and as probes. In addition, methods for the detection of a nucleic acid in a sample are disclosed wherein the oligomeric compounds are used. The hexitol structure provides as a particularly advantageous property a hydrophilic skeletal structure. Moreover, the hexitol and the cyclohexene structure is amenable to efficient chemical synthesis, has an enhanced stability versus degradation by nucleases and is stable against depurination.

Conventional techniques of molecular biology and nucleic acid chemistry, which are within the skill of the art, are explained in the literature. See, for example, Sambrook et al., Molecular Cloning: A Laboratory Manual, Cold Spring Harbor Laboratory, Cold Spring Harbor, N.Y., 1989; Gait, M. J., Oligonucleotide Synthesis, ed. (1984); Hames, B. D., and Higgins, S. J., Nucleic Acid Hybridization, eds. (1984); and a series, Methods in Enzymology, Academic Press, Inc., all of which are incorporated herein by reference. All patents, patent applications, and publications mentioned herein, both supra and infra, are incorporated herein by reference.

As is known in the art, a "nucleoside" is a base-sugar combination. The base portion of the nucleoside is normally a heterocyclic base. The two most common classes of such (heterocyclic) bases are the purines and the pyrimidines which are natural (heterocyclic) bases, i.e. they occur naturally. In more detail, important natural (heterocyclic) bases are guanine, cytosine, thymine, adenine, uracil or even methylcytosine.

"Nucleotides" are "nucleosides" that further include a phosphate group covalently linked to the sugar portion of the nucleoside. For those "nucleosides" that include a pentofuranosyl sugar, the phosphate group can be linked to either the 2', 3' or 5' hydroxyl moiety of the sugar. A "nucleotide" is the "monomeric unit" of an "oligonucleotide", more generally denoted herein as an "oligomeric compound", or a "polynucleotide", more generally denoted as a "polymeric compound". Another general expression therefor is deoxyribonucleic acid (DNA) and ribonucleic acid (RNA).

"Modified nucleotides" (or "nucleotide analogs") differ from a natural "nucleotide" by some modification but still consist of a (heterocyclic) base, a pentofuranosyl sugar, a phosphate portion, (heterocyclic) base-like, pentofuranosyl sugar-like and phosphate-like portion or combinations thereof. A pentofuranosyl sugar-like portion is for example the 1,5 anhydrohexitol or cyclohexenyl moiety. For example, a "label" may be attached to the base portion of a "nucleotide" whereby a "modified nucleotide" is obtained. A natural (heterocyclic) base in a "nucleotide" may also be replaced by a non-natural (heterocyclic) base, i.e. a (heterocyclic) base that does not occur in nature, whereby a "modified nucleotide" is obtained as well. Then the "modified nucleotide contains a (heterocyclic) base-like portion or "base analog" which resembles a natural (heterocyclic) base. A "base analog" does not normally appear in nature, i.e. is non-natural in other words, but can substitute for the ones which do, despite minor differences in structure. According to the invention, a heterocyclic base may be natural or non-natural. The terms "modified nucleotide" or "nucleotide analog" are used interchangeably in the present application.

A "modified nucleoside" (or "nucleoside analog") differs from a natural nucleoside by some modification in the manner as outlined above for a "modified nucleotide" (or a "nucleotide analog").

A "non-nucleotide compound" is different from a natural "nucleotide" but is in the sense of this invention still capable—similar to a "nucleotide"—of being a "monomeric unit" of an "oligomeric compound". Therefore, a "non-nucleotide compound" has to be capable of forming an "oligomeric compound" with "nucleotides". Even "non-nucleotide compounds" may contain a base-like, pentofuranosyl sugar-like or a phosphate-like portion, however, not all of them are present at the same time in a "non-nucleotide compound".

According to the invention, an "oligomeric compound" is a compound consisting of "monomeric units" which may be "nucleotides" alone or "non-natural compounds", more specifically "modified nucleotides" (or "nucleotide analogs") or "non-nucleotide compounds", alone or combinations thereof. "Oligonucleotides" and "modified oligonucleotides" (or "oligonucleotide analogs") are subgroups of "oligomeric compounds" in the context of the invention.

In the context of this invention, the term "oligonucleotide" refers to "polynucleotides" formed from a plurality of "nucleotides" as the "monomeric unit", i.e. an "oligonucleotide" belongs to a specific subgroup of an "oligomeric compound" or "polymeric compound" of ribonucleic acid (RNA) or deoxyribonucleic acid (DNA) with "monomeric units". According to this invention, the term "oligonucleotide" only includes "oligonucleotides" composed of naturally-occurring "nucleotides". The phosphate groups are commonly referred to as forming the internucleoside backbone of the "oligonucleotide". The normal linkage or backbone of RNA and DNA is a 3' to 5' phosphodiester linkage.

A "modified oligonucleotide" (or "oligonucleotide analog") belongs to another specific subgroup of the "oligomeric compounds" that possesses one or more "nucleotides", one or more "non-nucleotide compounds" or "modified nucleotides" as "monomeric units". Thus, the terms "modified oligonucleotide" (or "oligonucleotide analog") refers to structures that function in a manner substantially similar to "oligonucleotides" and are used interchangeably throughout the application. From a synthetic point of view, a "modified oligonucleotide" (or a "oligonucleotide analog") can be for example made by chemical modification of "oligonucleotides" by appropriate modification of the phosphate backbone, ribose unit or the nucleotide bases (Uhlmann and Peyman, Chemical Reviews 90 (1990) 543; Verma, S., and Eckstein, F., Annu. Rev. Biochem. 67 (1998) 99-134). Representative modifications include phosphorothioate, phosphorodithioate, methyl phosphonate, phosphotriester or phosphoramidate inter-nucleoside linkages in place of phosphodiester inter-nucleoside linkages; deaza or aza purines and pyrimidines in place of natural purine and pyrimidine bases, pyrimidine bases having substituent groups at the 5 or 6 position; purine bases having altered substituent groups at the 2, 6 or 8 positions or 7 position as 7-deazapurines; sugars having substituent groups at, for example, their 2' position; or carbocyclic or acyclic sugar analogs. Other modifications consistent with the spirit of this invention are known to those skilled in the art. Such "modified oligonucleotides" (or "oligonucleotide analogs") are best described as being functionally interchangeable with, yet structurally different from, natural "oligonucleotides" (or synthetic "oligonucleotides" along natural lines). In more detail, exemplary modifications are disclosed in Verma, S., and Eckstein, F., Annu. Rev. Biochem. 67 (1998) 99-134 or WO 02/12263. In addition, modification can be made wherein nucleoside units are joined through groups that substitute for the internucleoside phosphate or sugar phosphate linkages. Such linkages include those disclosed in Verma, S., and Eckstein, F., Annu. Rev. Biochem. 67 (1998) 99-134. When other than phosphate linkages are utilized to link the nucleoside units, such structures have also been described as "oligonucleosides".

"Oligomeric compounds" as "oligonucleotides" and "modified oligonucleotides" according to the invention may be synthesized as principally described in the art and known to the expert in the field. Methods for preparing oligomeric compounds of specific sequences are known in the art, and include, for example, cloning and restriction of appropriate sequences where appropriate and direct chemical synthesis. Chemical synthesis methods may include, for example, the phosphotriester method described by Narang, S. A., et al., Methods in Enzymology 68 (1979) 90-98, the phosphodiester method disclosed by Brown, E. L., et al., Methods in Enzymology 68 (1979)109-151, the phosphoramidite method disclosed in Beaucage, S. L., and Caruthers, M. H., et al., Tetrahedron Letters 22 (1981) 1859-1862, the H-phosphonate method disclosed in Garegg et al., Chem. Scr. 25 (1985) 280 and the solid support method disclosed in U.S. Pat. No. 4,458,066.

As said above, a "nucleic acid" is a polymeric compound of "nucleotides" as known to the expert skilled in the art. It is used herein to denote a "nucleic acid" in a sample which should be analyzed, i.e. the presence, non-presence or amount thereof in a sample should be determined. Therefore, in other words the "nucleic acid" is the target and can therefore be also denoted as "target nucleic acid". For example, if it has to be determined whether blood contains the human immunodeficiency virus, the "target nucleic acid" is the nucleic acid of the human immunodeficiency virus.

The term "primer" is used herein as known to the expert skilled in the art and refers to "oligomeric compounds" primarily to "oligonucleotides" but also to "modified oligonucleotides" that are able to "prime" DNA synthesis by a template-dependent DNA polymerase, i.e. the 3'-end of the e.g. oligonucleotide provides a free 3'-OH group whereto further "nucleotides" may be attached by a template-dependent DNA polymerase establishing 3' to 5' phosphodiester linkage whereby desoxynucleoside triphosphates are used and whereby pyrophosphate is released.

The term "probe" refers to synthetically or biologically produced nucleic acids (DNA or RNA) which, by design or selection, contain specific nucleotide sequences that allow them to hybridize under defined predetermined stringencies specifically (i.e., preferentially) to "target nucleic acids". A "probe" can be identified as a "capture probe" meaning that it "captures" the target nucleic acid so that it can be separated from undesirable materials which might obscure its detection. Once separation is accomplished, detection of the captured "target nucleic acid" can be achieved using a suitable procedure. "Capture probes" are often already attached to a solid phase. A specific example therefor is the microarray situation wherein a multitude of "capture probes" are attached to a "solid phase" which "captures" labeled cRNA or cDNA.

"Alkyl" groups are preferably chosen from alkyl groups containing from 1 to 10 carbon atoms, either arranged in linear, branched or cyclic form. The actual length of the alkyl group will depend on the steric situation at the specific position where the alkyl group is located. If there are steric constraints, the alkyl group will generally be smaller, the methyl and ethyl group being most preferred.

"Alkenyl" groups are preferably selected from alkenyl groups containing from 2 to 10 carbon atoms. For the selections similar considerations apply as for alkyl groups. They also can be linear, branched and cyclic. The most preferred alkenyl group is the ethylene group. There can be more than one double bond in the alkenyl group.

"Alkynyl" groups have preferably from 2 to 10 carbon atoms. Again, those carbon atoms can be arranged in linear, branched and cyclic manner. There can be more than one triple bond in the alkynyl group. The most preferred alkynyl group is propynyl.

All "alkyl", "alkenyl" and "alkynyl" groups can be either unsubstituted or substituted. Substitution by hetero atoms as outlined above will help to increase solubility in aqueous solutions.

A "protecting group" is a chemical group that is attached to a functional moiety (for example to the oxygen in a hydroxyl group, the nitrogen in an amino group or the sulfur in a thiol group, thereby replacing the hydrogen) to protect the functional group from reacting in an undesired way. A protecting group is further defined by the fact that it can be removed without destroying the biological activity of the molecule formed, here the binding of the nucleic acid binding compound to a nucleic acid. Suitable protecting groups are known to a man skilled in the art. Preferred protecting groups according to this invention are fluorenylmethoxycarbonyl (FMOC), dimethoxytrityl-(DMT), monomethoxytrityl-, trifluoroacetyl-, levulinyl-, or silyl- groups. Preferred protecting groups for example for hydroxyl groups at the 5'-end of a nucleotide or oligonucleotide are selected-, from the trityl groups, for example dimethoxytrityl (DMT). Preferred protecting groups at exocyclic amino groups in Formula I are acyl groups, most preferred the benzoyl group (Bz), phenoxyacetyl or acetyl or formyl, and the amidine protecting groups as e.g. the N,N-dialkylformamidine group, preferentially the dimethyl-, diisobutyl-, and the di-n-butylformamidine group. Preferred O-protecting groups are the aroyl groups, the diphenylcarbamoyl group, the acyl groups, and the silyl groups. Among these most preferred is the benzoyl group. Preferred silyl groups are the trialkylsilyl groups, like, trimethylsilyl, triethylsilyl and tertiary butyl-dimethyl-silyl. Another preferred silyl group is the trimethylsilyl-oxy-methyl group (TOM) (WO99/09044). Further, preferred protecting groups are ortho nitro-benzyl, 2-(4-nitrophenyl)ethoxycarbonyl (NPEOC), photoactivable compounds as 2-nitrophenyl-propyloxy-carbonyl (NPPOC) (Giegrich et al., Nucleosides & Nucleotides17 (1998) 1987) and allyloxycarbonyl.

"Labels", often referred to as "reporter groups", are generally groups that make a nucleic acid, in particular the "oligomeric compound" or the "modified oligonucleotide" according to the invention, as well as any nucleic acids bound thereto distinguishable from the remainder of the liquid, i.e. the sample (nucleic acids having attached a "label" can also be termed labeled nucleic acid binding compounds, labeled probes or just probes). "Haptens (such as biotin or digoxigenin), enzymes (such as alkaline phosphatase or peroxidase) or fluorescent dyes (such as fluorescein or rhodamine) have, among others, mainly proven to be suitable as non-radioactive indicator molecules or in other words as non-radioactive "labels". These "signal groups" or "labels" can be attached to or incorporated in nucleic acids by various methods. Preferred "labels" according to the invention are dyes as a fluorescein dye, a rhodamine dye, a cyanine dye, and a coumarin dye or haptens as biotin. By general definition, a "hapten" is a small molecule which is not by itself an immunogen (can cause an immune response), but has at least one element of an antigen and can combine with an antibody or another larger carrier molecule to become immunogenic.

The term "linking moiety" refers to a group of atoms which connect the moiety intended to be used (e.g. the "solid phase" or the "label") to the position of attachment at the "nucleotide", "modified nucleotide" or "non-nucleotide compound". This can be e.g. the base, sugar or phosphate moiety of a "nucleotide" or "modified nucleotide" or the base-like, sugar-like or phosphate-like moiety of a "non-nucleotide compound" or "modified nucleotide". The "linking moiety" will provide flexibility such that the "oligomeric compound" according to the invention, in particular the "modified oligonucleotide", can bind the "target nucleic acid" to be determined without major hindrance by the "solid phase" or "label". "Linking moieties", especially those that are not hydrophobic, for example based on consecutive ethylenoxy-units as disclosed in DE 3943522, are known to an expert skilled in the art. In the context of the invention a linking moiety contains a reactive group which is the point of attachment to e.g. the "solid phase" or the "label".

According to the invention, a "solid phase" may be controlled pore glass (CPG), polystyrene or silica gel as used for oligonucleotide synthesis.

As used herein, "fluorescence resonance energy transfer relationship" and similar terms refer to adjacent hybridization of an "oligomeric compound" labeled with a "donor fluorescent label" and another "oligomeric compound" labeled with an "acceptor fluorescent label" to a "target nucleic acid" such that the "donor fluorescent label" can transfer resonance energy to the "acceptor fluorescent label" such that the "acceptor fluorescent label" produces a measurable fluorescence emission. If the "donor fluorescent label" and "acceptor fluorescent label" are spaced apart by too great a distance, then the "donor fluorescent label" cannot transfer resonance energy to the "acceptor fluorescent label" such that the "acceptor fluorescent label" emits measurable fluorescence, and hence the "donor fluorescent label" and "acceptor fluorescent label" are not in resonance energy transfer relationship.

By "array" is meant an arrangement of addressable locations on a device (see e.g. U.S. Pat. Nos. 5,143,854, 6,022,963, 6,156,501, WO90/15070, WO 92/10092). The locations can be arranged in two dimensional arrays, three dimensional arrays, or other matrix formats. The number of locations can range from several to at least hundreds of thousands. Most importantly, each location represents a totally independent reaction site. Each location carries a nucleic acid as e.g. an "oligomeric compound", which can serve as a binding partner for a second nucleic acid, in particular a target nucleic acid. Methods for the manufacturing thereof are described in EP-A-0 476 014 and Hoheisel, J. D., TIBTECH (1997), Vol. 15,465-469, WO 89/10977, WO 89/11548, U.S. Pat. Nos. 5,202,231, 5,002,867, WO 93/17126). Further development has provided methods for making very large arrays of oligonucleotide probes in very small areas (U.S. Pat. No. 5,143,854, WO 90/15070, WO 92/10092). Microfabricated arrays of large numbers of oligonucleotide probes, called "DNA chips" offer great promise for a wide variety of applications (see e.g. U.S. Pat. Nos. 6,156,501 and 6,022,963).

In the context of this invention, "hybridization" shall mean hydrogen bonding, which may be Watson-Crick, Hoogsteen or reversed Hoogsteen hydrogen bonding, between complementary nucleotides. For example, adenine and thymine are complementary nucleobases which pair through the formation of hydrogen bonds. "Complementary," as used herein, also refers to sequence complementarity between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity such that stable and specific binding occurs between the oligonucleotide and the DNA or RNA target. It is understood that an oligonucleotide need not be 100% complementary to its target DNA sequence to be specifically hybridizable. An oligonucleotide is specifically hybridizable when binding of the oligonucleotide to the target DNA or RNA molecule interferes with the normal function of the target DNA or RNA, and there is a sufficient degree of complementarity to avoid non-specific binding of the oligonucleotide to non-target sequences under conditions in which specific binding is desired, i.e. under physiological conditions in the case of in vivo assays or therapeutic treatment, or in the case of in vitro assays, under conditions in which the assays are performed.

A "reactive group" is a group that is capable of reacting with and connecting to another group on another molecule. Preferred "reactive groups" are hydroxyl (—OH), carboxyl, amino or thiol groups.

DETAILED DESCRIPTION OF THE INVENTION

In an embodiment of the invention, compounds are provided that are capable of being incorporated into nucleic acids by chemical or enzymatic synthesis. Therefore, in an embodiment of the invention, a compound is provided according to Formula I:

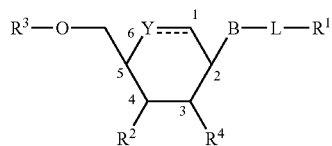

Formula I wherein L is a linking moiety,
wherein B is a heterocyclic base,
wherein $R^1$ is independent from $R^2, R^3, R^4, R^5, R^{5a}, R^{5b}$ and $R^6$ wherein $R^1$ is selected from the group consisting of a protecting group, a label, a solid phase, and —H,
wherein $R^2$ is independent from $R^1, R^3, R^4, R^5, R^{5a}, R^{5b}$, and $R^6$ wherein $R^2$ is selected from the group consisting of —H and —$OR^6$,
wherein $R^3$ is independent from $R^1, R^2, R^4, R^5, R^{5a}, R^{5b}$ and $R^6$ and wherein $R^3$ is selected from the group consisting of a protecting group, a linking moiety covalently coupled to a solid phase, a phosphoramidite, a H-phosphonate, and a triphosphate,
wherein $R^4$ is independent from $R^1, R^2, R^3, R^5, R^{5a}, R^{5b}$ and $R^6$ and $R^4$ is —H, —OH, alkyl, halogen, —O—$R^5$, —S—$R^5$, $NR^5R^{5a}$, a label or a linking moiety covalently coupled to a solid phase,
wherein $R^6$ is independent from $R^1, R^2, R^3, R^4, R^5, R^{5a}$, and $R^{5b}$, and wherein $R^6$ is selected from the group consisting of —H, a protecting group, a linking moiety covalently coupled to a solid phase, a phosphoramidite, and a H-phosphonate,
wherein the dotted line between the C1 atom of the six-membered ring and Y represents the optional presence of a double bond whereby Y is $CR^{5a}$ when the double bond is present, or Y is selected from the group consisting of O, S, $NR^5$ and $CR^{5a}R^{5b}$ when the double bond is absent,
whereby $R^5, R^{5a}$ and $R^{5b}$ are independent from one another and independent from $R^1, R^2, R^3, R^4$ and $R^6$ and $R^5$ is independently selected from alkyl, alkenyl, alkinyl, aryl, acyl, a protecting group or —H, and $R^{5a}$ and $R^{5b}$ are independently selected from alkyl, alkenyl, alkinyl, aryl, acyl, or —H.

Preferably, $R^6$ and $R^3$ are not both a solid phase, both a phosphoramidite, both a H-phosphonate, or a phosphoramidite and a H-phosphonate, or a solid phase and a phosphoramidite, or a solid phase and a H-phosphonate. Preferably, when one residue selected from the group consisting of $R^1, R^3$ or $R^6$ is a solid phase then the other two residues selected from the group consisting of $R^1, R^3$ or $R^6$ are not a solid phase. The expert skilled in the art is aware of the compounds exemplified in Formula I that do not make sense with regard to their property of being capable of being incorporated into nucleic acids.

In another preferred embodiment of the invention, $R^4$ in the Formula I of the compound according to the invention is —H or OH.

In a preferred embodiment, the heterocyclic base in the Formula I of the compound according to the invention is a natural or a non-natural heterocyclic base. Preferably, the natural heterocyclic base is adenine, guanine, cytosine, thymine, uracil or methyl-cytosine. More preferably the natural heterocyclic base is a pyrimidine or a 7-deazapurine, more preferably a uracil. Preferably, the C5 atom of pyrimidines, in particular uracil, or the 7-position of 7-deazapurines is the point of attachment of the linking moiety L.

The nature of the linking moiety L in Formula I is designed to space the group $R^1$ a sufficient distance from B such that (a) the compound according to the invention is able to be recognized by a polymerase and incorporated in a growing nucleic acid chain during a polymerization reaction, when R3 is a triphosphate;

(b) the compound according to the invention once incorporated in a nucleic acid chain, is preferably able to base pair to a complementary base, that is the hybridization ability of the probe produced by the amplification reaction should preferably not be significantly affected; and (c) the group $R^1$ is held away from the target nucleic acid to avoid interactions or quenching effects if no intercalation of the group $R^1$ is intended.

In another preferred embodiment, the linking moiety L in the compound according to the invention comprises carbon, oxygen or nitrogen atoms and a reactive group. Preferably the reactive group is a carboxyl, amino, thiol or hydroxyl group. L is preferably an optionally substituted and optionally interrupted hydrocarbon chain derivative and is preferably more than 2 carbon atoms, preferably more than 3 carbon atoms and preferably up to 30 carbon atoms long. The optional interruptions are —CH=CH—, —C≡C—, —NH—, —CONH—, —S—, —O—, —$SO_2$—, ureido, phenylene, cyclohexylene and groups of the formula —CH=CH—NH—, —CH=CH—$CH_2$—NH—, —NH—C(=$NH_2$)$^+$—, —NH—C(=$NH_2$)$^+$—NH— and —C(=O)—O—. For the avoidance of doubt 1,2-, 1,3- and 1,4-phenylene groups are respectively regarded as 2, 3 and 4 carbon atoms long. The optional interruptions are incorporated in order to facilitate the synthesis of the chain and/or to provide more hydrophilic elements to maintain the linear structure of the chain and prevent it folding in on itself. Preferably, the linking moiety is a derivative of a $C_1$-$C_{10}$ alkyl, a $C_2$-$C_{10}$ alkenyl, a $C_2$-$C_{10}$ alkynyl, an aminoallyl or an acrylamido moiety. More preferably, the linking moiety is a derivative of a $C_2$-$C_{10}$, $C_3$-$C_{10}$ or $C_4$-$C_{10}$ alkyl.

The site of attachment of the linking moiety L on the nucleoside triphosphate is on the base moiety. In order not to interfere with hybridization it is preferable that L should be joined to those atoms that are believed to be exposed in the major groove of the DNA double helix that is C5, C6 or the amino group on C4 of cytosine; C5, C6 or the oxygen attached to C4 of uridine; C5 methyl, C6 or the oxygen attached to C4 of thymine; N7, C8 or the amino group on C6 of adenine; N7, C8 or the oxygen attached to C6 of guanine or C7 of deaza-adenine or deaza-guanine.

In another embodiment, $R^1$ is independent from $R^2, R^3, R^4, R^5, R^{5a}, R^{5b}$ and $R^6$ wherein $R^1$ is a protecting group, a label, or a solid phase. In another embodiment, $R^1$ is independent from $R^2, R^3, R^4, R^5, R^{5a}, R^{5b}$ and $R^6$ wherein $R^1$ is a label or a solid phase. In another embodiment, $R^1$ is independent from $R^2, R^3, R^4, R^5, R^{5a}, R^{5b}$ and $R^6$ wherein $R^1$ is a protecting group or a label. In the most preferred embodiment, $R^1$ in the Formula I of the compound according to the invention is a label.

Preferably, the label is a dye or a hapten, preferably a fluorescent dye. Preferably, the dye is selected from the group consisting of a fluorescein dye, a rhodamine dye, a cyanine dye, a coumarin dye, and an azo dye. Preferably, the hapten is biotin.

According to the invention, preferred compounds are compounds which can be easily incorporated into nucleic acids by the use of enzymes. Therefore, in a very preferred embodiment, $R^3$ is a triphosphate, $R^2$ is —$OR^6$, wherein $R^6$ is —H, and $R^4$ is —H or —OH in the Formula I of the compound according to the invention.

In another very preferred embodiment of the invention, Y is O, S, or $CR^{5a}R^{5b}$ when the double bond is absent in the Formula I of the compounds according to the invention. Most preferred, Y is O. Very preferred compounds according to the invention are represented by Formula II:

In a preferred embodiment of the invention, an oligomeric compound with an monomeric unit with Formula III is provided:

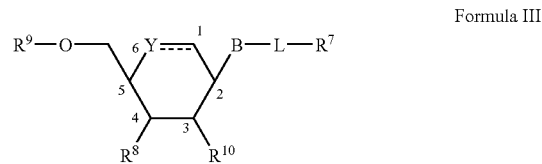

Formula III wherein L is a linking moiety covalently and B is a heterocyclic base,

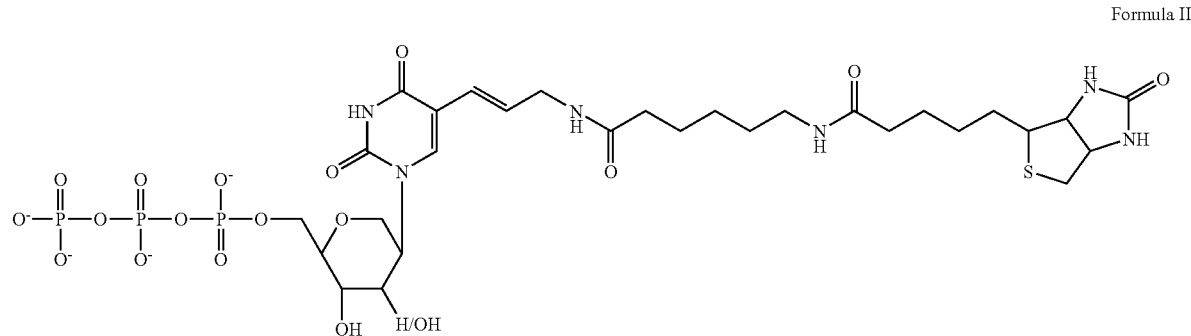

Formula II

The term "H/OH" shall denote that —H or —OH may be present, in other words it could be described as residue K which can be —H or —OH.

In another very preferred embodiment of the invention, cyclohexene derivatives are provided, i.e. the dotted line between the C1 atom of the six-membered ring and Y represents the presence of a double bond in the Formula I of the compound according to the invention whereby Y is $CR^{5a}$ and $R^{5a}$ is independently selected from alkyl, alkenyl, alkinyl, aryl, acyl, or —H. Preferably, $R^{5a}$ is —H.

In a preferred embodiment of the invention, a phosphoramidite is provided suitable for chemical synthesis of oligomeric compounds according to the invention. This is more specifically a compound according to the invention with Formula I, wherein $R^2$ is independent from $R^1$, $R^3$, $R^4$, $R^5$, $R^{5a}$, $R^{5b}$, and $R^6$ and $R^2$ is —$OR^6$ wherein $R^6$ is a phosphoramidite; and $R^3$ is independent from $R^1$, $R^2$, $R^4$, $R^5$, $R^{5a}$, $R^{5b}$ and $R^6$ and $R^3$ is a protecting group or a solid phase covalently coupled to a linking moiety. Preferably, $R^3$ is a protecting group.

In another embodiment of the invention, an oligomeric compound comprising a monomeric unit with the formula S—B—L—$R^7$ is provided wherein S is a moiety comprising a six-membered ring, B is a heterocyclic base, L is a linking moiety, and $R^7$ is a label, a protecting group or a solid phase. Preferably, the six-membered ring is a derivative of cyclohexane, cyclohexene, tetrahydropyran, tetrahydrothiopyran or piperidine. Preferably, $R^7$ is a label or a solid phase, more preferably $R^7$ is a label.

wherein $R^7$ is independent from $R^5$, $R^{5a}$, $R^{5b}$, $R^8$, $R^9$, $R^{10}$, and $R^{11}$ wherein $R^7$ is selected from the group consisting of a protecting group, a label, a solid phase, and —H, wherein $R^8$ is independent from $R^5$, $R^{5a}$, $R^{5b}$, $R^7$, $R^9$, $R^{10}$, and $R^{11}$ and wherein $R^8$ is selected from the group consisting of —H and —$OR^{11}$, wherein $R^9$ and $R^{11}$ are independent from each other and independent from $R^5$, $R^{5a}$, $R^{5b}$, $R^7$, $R^8$ or $R^{10}$, and wherein $R^9$ and $R^{11}$ are selected from the group consisting of —H, a linking moiety covalently coupled to a solid phase, a phosphate, a phosphodiester with a nucleotide, a modified nucleotide, an oligonucleotide or a modified oligonucleotide, wherein $R^{10}$ is independent from $R^5$, $R^{5a}$, $R^{5b}$, $R^7$, $R^8$, $R^9$ and $R^{11}$ and $R^{10}$ is —H, —OH, alkyl, halogen, —O—$R^5$, —S—$R^5$, $NR^5R^{5a}$, a label or a linking moiety covalently coupled to a solid phase, wherein the dotted line between the C1 atom of the six-membered ring and Y represents the optional presence of a double bond whereby Y is $CR^{5a}$ when the double bond is present, or Y is selected from the group consisting of O, S, $NR^5$ and $CR^{5a}R^{5b}$ when the double bond is absent, whereby $R^5$, $R^{5a}$ and $R^{5b}$ are independent from one another and independent from $R^7$, $R^8$, $R^9$, $R^{10}$ and $R^{11}$ and $R^5$ is independently selected from alkyl, alkenyl, alkinyl, aryl, acyl, a protecting group or —H and $R^{5a}$ and $R^{5b}$ are independently selected from alkyl, alkenyl, alkinyl, aryl, acyl, or —H.

Preferably, $R^8$ and $R^9$ are not both —H or $R^9$ and $R^{11}$ are not both —H when $R^8$ is $OR^{11}$ to exclude the case that only a monomer is considered. The expert skilled in the art is aware of the compounds that would be senseless according to the invention, i.e. $R^9$ and $R^{11}$ are not both phosphate or —H and a phosphate. Preferably, when one residue selected from the group consisting of $R^7$, $R^9$, $R^{10}$ or $R^{11}$ is a solid phase or a linking moiety covalently coupled to a solid phase then the other residues selected from the group consisting of $R^7$, $R^9$, $R^{10}$ or $R^{11}$ are not a solid phase or a linking moiety covalently coupled to a solid phase.

The phosphate or triphosphate residues may also be modified phosphate or analogs of phosphate as e.g. thiophosphates or α-thio-triphosphates.

In a preferred embodiment, the heterocyclic base in the Formula III of the oligomeric compound according to the invention is a natural or a non-natural heterocyclic base. Preferably, the natural heterocyclic base is adenine, guanine, cytosine, thymine, uracil or methyl-cytosine. More preferably the natural heterocyclic base is a pyrimidine or a 7-deazapurine, more preferably an uracil. Preferably, the C5 atom of pyrimidines, in particular uracil, or the 7-position of 7-deazapurines is the point of attachment of the linking moiety L.

Preferably $R^7$ is a label or a solid phase, more preferably $R^7$ is a label.

The nature of the linking moiety L in Formula I is designed to space the group $R^1$ a sufficient distance from B such that
  (a) the compound according to the invention is able to be recognized by a polymerase and incorporated in a growing nucleic acid chain during a polymerization reaction, when R3 is a triphosphate;
  (b) the compound according to the invention once incorporated in a nucleic acid chain, is preferably able to base pair to a complementary base, that is the hybridization ability of the probe produced by the amplification reaction should preferably not be significantly affected; and
  (c) the group $R^1$ is held away from the target nucleic acid to avoid interactions or quenching effects if no intercalation of the group $R^1$ is intended.

In another preferred embodiment, the linking moiety L in the compound according to the invention comprises carbon, oxygen or nitrogen atoms and a reactive group. Preferably the reactive group is a carboxyl, amino, thiol or hydroxyl group. L is preferably an optionally substituted and optionally interrupted hydrocarbon chain derivative and is preferably more than 2 carbon atoms, preferably more than 3 carbon atoms and preferably up to 30 carbon atoms long. The optional interruptions are —CH=CH—, —C≡C—, —NH—, —CONH—, —S—, —O—, —SO$_2$—, ureido, phenylene, cyclohexylene and groups of the formula —CH=CH—NH—, —CH=CH—CH$_2$—NH—, —NH—C(=NH$_2$)$^+$—, —NH—C(=NH$_2$)$^+$—NH— and —C(=O)—O—. For the avoidance of doubt 1,2-, 1,3- and 1,4-phenylene groups are respectively regarded as 2, 3 and 4 carbon atoms long. The optional interruptions are incorporated in order to facilitate the synthesis of the chain and/or to provide more hydrophilic elements to maintain the linear structure of the chain and prevent it folding in on itself. Preferably, the linking moiety is a derivative of a $C_1$-$C_{10}$ alkyl, a $C_2$-$C_{10}$ alkenyl, a $C_2$-$C_{10}$ alkynyl, an aminoallyl or an acrylamido moiety. More preferably, the linking moiety is a derivative of a $C_2$-$C_{10}$, $C_3$-$C_{10}$ or $C_4$-$C_{10}$ alkyl.

The site of attachment of the linking moiety L on the nucleoside triphosphate is on the base moiety. In order not to interfere with hybridization it is preferable that L should be joined to those atoms that are believed to be exposed in the major groove of the DNA double helix that is C5, C6 or the amino group on C4 of cytosine; C5, C6 or the oxygen attached to C4 of uridine; C5 methyl, C6 or the oxygen attached to C4 of thymine; N7, C8 or the amino group on C6 of adenine; N7, C8 or the oxygen attached to C6 of guanine or C7 of deaza-adenine or deaza-guanine.

In another preferred embodiment, $R^7$ in Formula III of the compound according to the invention is a label. Preferably, the label is a dye or a hapten, preferably a fluorescent dye. More preferably, the dye is selected from the group consisting of a fluorescein dye, a rhodamine dye, a cyanine dye, a coumarin dye, and an azo dye. Preferably, the hapten is biotin.

In a very preferred embodiment of the invention, the compound is a modified oligonucleotide, whereby in Formula III of the compound according to the invention $R^8$ is —$OR^{11}$, and $R^9$ and $R^{11}$ is an oligonucleotide or a modified oligonucleotide and $R^{10}$ is —H or —OH.

In a preferred embodiment of the invention, Y is O, S or $CR^{5a}R^{5b}$ when the double bond is absent. In a very preferred embodiment of the invention, the compound according to the invention is a hexitol derivative, i.e. Y is O in Formula III of the compound according to the invention when the double bond is absent.

In a very preferred embodiment of the invention, the compound according to the invention is a cyclohexenyl derivative, i.e. the dotted line between the C1 atom of the six-membered ring and Y represents the presence of a double bond whereby Y is $CR^{5a}$ and $R^{5a}$ is independently selected from alkyl, alkenyl, alkinyl, aryl, acyl, or —H. Preferably, $R^{5a}$ is —H.

For use in the formats used in the LightCycler® Instrument, the compound according to the invention will be preferably directed to the 3'- or 5'-end of the oligomeric compound during the synthesis thereof.

Preferably for use in the TaqMan® format, the label $R^7$ attached to the oligomeric compound according to the invention may be located internally in the oligomeric compound according to the invention, at the 5'-end or the 3'-end of the oligomeric compound according to the invention.

The label is preferably a fluorescent label, preferably a fluorescein or a rhodamine dye. The oligomeric compound according to the invention may further comprise other labels wherein the emission wavelengths of one of the labels overlap the absorption wavelengths of another of the labels. Preferably, the oligomeric compound further comprises a second label acting as a quenching agent that quenches the fluorescence emission of the fluorescent label, which can be fluorescein. Preferably the quenching agent is a fluorescent rhodamine or cyanine dye or a non-fluorescent label as dabcyl ("Dark quencher"). In the most preferred embodiment, the oligomeric compound according to the invention cannot be extended enzymatically to be used as probe in the TaqMan® format as principally set out in U.S. Pat. Nos. 5,210,015, 5,487,972 or 5,804,375. Preferably, the monomeric unit at the 3'-end of the oligomeric compound is a 2',3'-dideoxynucleotide or a 3'-phosphorylated nucleotide. Preferably for use in the TaqMan® format, the monomeric unit according to the invention with a label, preferably a fluorescent label, as well as a second monomeric unit with another label, preferably a second fluorescent label, may be located internally in the oligomeric compound according to the invention or at the 5'-end and/or 3'-end of the oligomeric compound according to the invention. Therefore, in a preferred embodiment of the invention, the oligomeric compound according to the invention comprises a modified oligonucleotide that comprises a monomeric unit that is a linking moiety with a second label attached to a nucleotide, or a linking moiety with a second label attached to a modified nucleotide or a non-nucleotide compound.

Preferably, the second label is a second dye which is preferably fluorescent and is preferably selected from the group consisting of a fluorescein dye, a rhodamine dye, a cyanine dye, a coumarin dye, and an azo dye.

Preferably, the oligomeric compound according to the invention cannot be extended enzymatically. Therefor, preferably the monomeric unit at the 3'-end of the oligomeric compound is a 2',3'-dideoxy-nucleotide or a 3'-phosphorylated nucleotide.

The expert skilled in the art acknowledges the fact that the six-membered ring of the compound according to the invention or of the oligomeric compound according to the invention may carry further substituents and still be functional in the methods according to the invention. In particular the six-membered ring but also the linking moiety may carry further halogen, thiol, hydroxyl, amino, alkyl, alkenyl, alkynyl, aryl substituents whereby alkyl, alkenyl, alkynyl, aryl substituents may optionally contain heteroatoms or heteroaryl substituents optionally substituted with further substituents. Preferred is also a further substituent at the C5 atom of the six-membered ring of Formula I or III which is selected from alkyl, alkenyl, alkynyl, aryl, alkoxy, aminoalkyl, halogen, azido, hydroxyl, carboxyl or an amino moiety. These compounds may be tested whether they can be used in the methods or uses according to the invention by e.g. simple hybridization experiments with complementary oligonucleotides as described, in the assay formats used in the LightCycler® instrument or in the TaqMan® instrument or in the chemical synthesis method according to the invention making use of phosphoramidite or solid phase-linked compounds.

The oligomeric compounds according to the invention may be synthesized as principally described in the art and known to the expert in the field, particularly preferred building blocks therefor are the compounds according to the invention. Methods for preparing oligomeric compounds as oligonucleotides and modified oligonucleotides of specific sequences are known in the art, and include, for example, cloning and restriction of appropriate sequences and direct chemical synthesis. Chemical synthesis methods may include, for example, the phosphotriester method described by Narang, S. A., et al., Methods in Enzymology 68 (1979) 90-98, the phosphodiester method disclosed by Brown, E. L., et al., Methods in Enzymology 68 (1979) 109-151, the phosphoramidite method disclosed in Beaucage et al., Tetrahedron Letters 22 (1981) 1859, the H-phosphonate method disclosed in Garegg et al., Chem. Scr. 25 (1985) 280, and the solid support method disclosed in U.S. Pat. No. 4,458,066. Particularly preferred is the phosphoramidite method. Therefore, in another embodiment of the invention, a method for the chemical synthesis of an oligomeric compound according to the invention is provided, comprising the steps of (a) providing a compound according to the invention, wherein $R^2$ is —$OR^6$ and $R^6$ is phosphoramidite and $R^3$ is a protecting group, (b) providing an —OH group of a nucleoside or a modified nucleoside bound to a solid phase by another —OH group, or providing an —OH group of an oligonucleotide or a modified oligonucleotide bound to a solid phase by another —OH group of the nucleotide or modified nucleotide at the 3'-end of the oligonucleotide or the modified oligonucleotide, (c) reacting the phosphorous atom of the phosphoramidite with the free OH group to form a phosphite ester and oxidizing the phosphite ester to a phosphotriester, (d) optionally reacting any unreacted —OH group of step (c) with another compound to prevent any further reactions of the unreacted 5'-OH group of step (c) in the following steps ("Capping"-reaction), (e) optionally repeating steps (c) to (d) with phosphoramidite derivatives of nucleosides, modified nucleosides or a compound according to the invention, wherein $R^2$ is —$OR^6$ and $R^6$ is phosphoramidite and $R^3$ is a protecting group after removal of the hydroxyl protecting group of the product of step (d) to provide a free —OH group, and (f) cleaving the oligomeric compound from the solid phase, removing the protecting groups and thereby converting the phosphotriester to a phosphodiester, and (g) isolating the oligomeric compound.

Methods for performing these reaction steps are known to the expert skilled in the art.

In another preferred embodiment of the invention, a method for the enzymatic synthesis of an oligomeric compound according to the invention is provided comprising the steps of (a) incubating a compound according to the invention, wherein $R^3$ of said compound is a triphosphate, with an OH group, which is preferably extendable, of the nucleotide or modified nucleotide at the 3'-end of a polynucleotide, oligonucleotide or a modified oligonucleotide in the presence of a terminal transferase or a polymerase, whereby the compound is attached to the OH group, which is preferably extendable, whereby pyrophosphate is released, (b) optionally incubating the OH group, which is preferably extendable, at the 3'-end of the product of step (a) with a nucleoside triphosphate or a modified nucleoside triphosphate in the presence of terminal transferase or a polymerase, whereby the nucleotide or modified nucleotide is attached to the OH group, which is preferably extendable, whereby pyrophosphate is released, (c) optionally repeating step (a) or (b) or both, and (d) isolating the oligomeric compound.

In the case of the use of terminal transferase, step (b) and (c) of the method for the enzymatic synthesis according to the invention are preferably not performed.

In another preferred embodiment of the invention, a composition for analyzing interactions between target nucleic acids and oligomeric compounds comprising an array of a plurality of oligomeric compounds according to the invention having different sequences. Most preferred, the oligomeric compound is an oligomeric compound according to the invention, i.e. it is a compound with Formula III wherein $R^7$ is the solid phase or $R^9$, $R^{10}$ or $R^{11}$ is a linking moiety covalently coupled to the solid phase, i.e. these residues are the point of attachment to the solid phase.

In a preferred embodiment of the invention, a compound according to the invention with Formula I, wherein $R^2$ is —$OR^6$ and $R^6$ is a phosphoramidite, and $R^3$ is a solid phase covalently coupled to a linking moiety or a protecting group, is used for the chemical synthesis of an oligomeric compound according to the invention.

In another preferred embodiment of the invention, a compound according to the invention is used for the labeling of nucleic acids, i.e. the enzymatic incorporation of labeled modified nucleotides into nucleic acids whereby the method for the enzymatic synthesis of an oligomeric compound according to the invention is used employing triphosphate derivatives of the compound according to the invention. In more detail, a compound according to the invention with Formula I, wherein $R^3$ is a triphosphate, $R^2$ is —$OR^6$, wherein $R^6$ is —H, and $R^4$ is —H or —OH is used for the enzymatic synthesis of a labeled nucleic acid, i.e. an oligomeric compound according to the invention.

In yet another preferred embodiment, an oligomeric compound according to the invention or a composition according to the invention is used in a hybridization reaction with a complementary nucleic acid, e.g. the hybridization of an oligomeric compound according to the invention to a plurality of oligonucleotides bound to a solid phase at predefined locations to form a microarray. In even another preferred embodiment, an oligomeric compound according to the invention is used as a primer, probe or capture probe. The incorporation of compounds according to the invention comprising six-membered rings into oligomeric compounds is particularly useful for the stabilisation of an oligomeric compound according to the invention against the digestion by nucleases and depurination of purine bases.

In yet another preferred embodiment of the invention, an oligomeric compound according to the invention is provided that is attached to a solid phase and that is preferably a compound with Formula III. This is particularly preferred for sequence-specific capturing of RNA as hexitol nucleic acids primarily bind to RNA (Lescrinier, E., et al., Chem. Biol. 7 (2000) 719-731).

In another embodiment of the invention a method for the detection of a target nucleic acid in a sample is provided comprising the steps of
  (a) providing a sample suspected to contain the target nucleic acid
  (b) providing an oligomeric compound according to the invention, which is essentially complementary to a part or all of the target nucleic acid,
  (c) optionally amplifying the target nucleic acid with a template-dependent DNA polymerase and primers
  (c) contacting the sample with the oligomeric compound under conditions for binding the oligomeric compound to the target nucleic acid,
  (d) determining the binding product or the degree of hybridization between the target nucleic acid and the oligomeric compound as a measure of the presence, absence or amount of the target nucleic acid.

Preferably in step (d) of the method, the degree of hybridization is determined by the quantity of the first or second fluorescent label that is released from the oligomeric compound hybridized to the target nucleic acid by exonuclease hydrolysis by the template-dependent DNA polymerase. Therefor, preferably, an oligomeric compound according to the invention comprises two labels, preferably two fluorescent labels.

The amplification is performed preferably with the polymerase chain reaction which specifically amplifies target nucleic acids to detectable amounts. Other possible amplification reactions are the Ligase Chain Reaction (LCR; Wu, D. Y., and Wallace, R. B., Genomics 4 (1989) 560-569; and Barany, F., Proc. Natl. Acad. Sci. USA 88 (1991)189-193); Polymerase Ligase Chain Reaction (Barany, F., PCR Methods and Appl. 1 (1991) 5-16); Gap-LCR (WO 90/01069); Repair Chain Reaction (EP 0439182), 3SR (Kwoh, D. Y., et al., Proc. Natl. Acad. Sci. USA 86 (1989) 1173-1177; Guatelli, J. C., et al., Proc. Natl. Acad. Sci. USA 87 (1990) 1874-1878; WO 92/08808), and NASBA (U.S. Pat. No. 5,130,238). Further, there are strand displacement amplification (SDA), transcription mediated amplification (TMA), and Qβ-amplification (for a review see e.g. Whelen, A. C., and Persing, D. H., Annu. Rev. Microbiol. 50 (1996) 349-373; Abramson, R. D., and Myers, T. W., Current Opinion in Biotechnology 4 (1993) 41-47).

The preferred template-dependent DNA polymerase is Taq polymerase.

In a preferred embodiment of the method for the detection of a target nucleic acid, the format used in the TaqMan® assay is contemplated whereby the oligomeric compound according to the invention is used as a probe. Therefor, the oligomeric compound according to the invention comprises a label as $R^7$ which is preferably a fluorescent label, preferably fluorescein. The oligomeric compound according to the invention may further comprise other fluorescent labels wherein the emission wavelengths of one of the fluorescent labels overlap the absorption wavelengths of another of the fluorescent labels. Preferably, the oligomeric compound further comprises a second fluorescent label acting as a quenching agent that quenches the fluorescence emission of the fluorescent label, which can be fluorescein. Preferably the quenching agent is a fluorescent rhodamine or cyanine. The quenching agent can also be a non-fluorescent compound or dye as dabcyl ("Dark quencher"). The oligomeric compound according to the invention cannot be extended enzymatically to be used as probe in the TaqMan® format as principally set out in U.S. Pat. Nos. 5,210,015, 5,487,972, or 5,804,375. Preferably, the monomeric unit at the 3'-end of the oligomeric compound is a 2',3'-dideoxynucleotide or a 3'-phosphorylated nucleotide. Preferably for use in the TaqMan® format, the compound according to the invention with a label as well as a second compound with the label may be located internally in the modified oligonucleotide according to the invention or at the 5'-end and/or 3'-end of the modified oligonucleotide according to the invention. In consequence for the format used in the TaqMan® assay, in the determination step of the method, the spatial relationship between the fluorescent label and the second label, i.e. the quenching agent, subsequent to hybridization is altered, preferably by exonuclease hydrolysis of a template-dependent DNA polymerase, preferably the Taq-Polymerase, of the nucleic acid binding compound whereby release of label occurs as a result of exonuclease hydrolysis. The degree of hybridization between the oligomeric compound according to the invention and the target nucleic acid is determined by the quantity of label that is released from the oligomeric compound according to the invention subsequent to hybridization. Therefore it is a preferred embodiment of the invention that in step (d) the degree of hybridization is determined by the quantity of label that is released from the oligomeric compound hybridized to the nucleic acid by exonuclease hydrolysis by the template-dependent DNA polymerase.

In a very preferred embodiment of the invention related in more detail to the TaqMan® assay format, a method for the detection of a target nucleic acid in a sample is provided comprising the steps of
  (a) contacting a sample comprising single-stranded nucleic acids with an oligonucleotide containing a sequence complementary to a region of the target nucleic acid and an oligomeric compound according to the invention, whereby $R^7$ is a fluorescent label and the oligomeric compound contains a second fluorescent label, and whereby said oligomeric compound contains a sequence complementary to a second region of the same target nucleic acid sequence strand, but not including the nucleic acid sequence defined by the oligonucleotide, to create a mixture of duplexes during hybridization conditions, wherein the duplexes comprise the target nucleic acid annealed to the oligonucleotide and to the oligomeric compound such that the 3' end of the first oligonucleotide is upstream of the 5' end of the oligomeric compound, (b) maintaining the mixture of step (a) having a 5' to 3' nuclease activity under conditions sufficient to permit the 5' to 3' nuclease activity of the polymerase to cleave the annealed, oligomeric compound and release labeled fragments; and (c) detecting and/or measuring the release of labeled fragments.

In another embodiment of the invention, a format for the use in the LightCycler® instrument is provided as described in U.S. Pat. No. 6,174,670. For use in the formats used in the LightCycler® Instrument, the compound according to invention will be preferably at the 3'- or 5'-end, i.e. the monomeric unit at the 3'- or 5'-end of the oligomeric compound after the synthesis thereof. These formats apply the fluorescent resonance energy transfer technology (see, for example, U.S. Pat. Nos. 4,996,143, 5,565,322, 5,849,489, and 6,162,603) and are based on the fact that when a donor and a corresponding acceptor fluorescent label are positioned within a certain distance of each other, energy transfer takes place between the two fluorescent labels that can be visualized or otherwise detected and/or quantitated. As used herein, two probes, each containing a fluorescent label, whereby at least one thereof is an oligomeric compound according to the invention, can hybridize to an amplification product at particular positions determined by the complementarity of the probes to the target nucleic acid. The fluorescent label according to the invention of the oligomeric compound according to the invention may be a donor or acceptor fluorescent label. Upon hybridization of the probes to the amplification product at the appropriate positions, a FRET signal is generated. Fluorescent analysis can be carried out using, for example, a photon counting epifluorescent microscope system (containing the appropriate dichroic mirror and filters for monitoring fluorescent emission at the particular range), a photon counting photomultiplier system, or a fluorometer. Excitation to initiate energy transfer can be carried out with an argon ion laser, a high intensity mercury (Hg) arc lamp, a fiber optic light source, or other high intensity light source appropriately filtered for excitation in the desired range. As used herein with respect to donor and corresponding acceptor fluorescent labels, "corresponding" refers to an acceptor fluorescent label having an excitation spectrum that overlaps the emission spectrum of the donor fluorescent label. Accordingly, efficient non-radiative energy transfer can be produced there between. The preferred fluorescent label is fluorescein as the donor fluorescent label, whereby the acceptor fluorescent label is rhodamine, however, preferred is a cyanine dye, preferably Cy5 as described in U.S. Pat. No. 6,174,670.

Therefore, in an embodiment of the invention, a method for detecting the presence or absence of a target nucleic acid in a sample is provided, comprising the steps of:

(a) performing at least one cycling step, wherein a cycling step comprises an amplifying step and a hybridizing step, wherein said amplifying step comprises contacting said sample with primers to produce an amplification product if target nucleic acid is present in said sample, wherein said hybridizing step comprises contacting said sample with a pair of probes, wherein the members of said pair of probes hybridize to said amplification product within no more than five nucleotides of each other, wherein a first probe of said pair of probes is labeled with a donor fluorescent label and wherein a second probe of said pair of probes is labeled with a corresponding acceptor fluorescent label, and whereby one of the probes is an oligomeric compound according to the invention, and (b) detecting the presence or absence of fluorescence resonance energy transfer between said donor fluorescent label of said first probe and said acceptor fluorescent label of said second probe, wherein the presence of FRET is indicative of the presence of the target nucleic acid in the sample, and wherein the absence of FRET is indicative of the absence of the target nucleic acid in the sample.

Therefore, in a preferred embodiment of the invention, a method for detecting a target nucleic acid in a sample is provided, comprising the steps of amplifying the nucleic acid by polymerase chain reaction in the presence of two nucleic acid probes, whereby a probe is an oligomeric compound according to the invention, that hybridize to adjacent regions of the target nucleic acid, one of said probes being labeled with an acceptor fluorescent label and the other probe labeled with a donor fluorescent label of a fluorescence energy transfer pair such that upon hybridization of the two probes with the target nucleic acid, the donor and acceptor fluorescent labels are within 25 nucleotides of one another, said polymerase chain reaction comprising the steps of adding a thermostable polymerase, nucleotides and primers for the target nucleic acid to the sample and thermally cycling the sample between at least a denaturation temperature and an elongation temperature; exciting the biological sample with light at a wavelength absorbed by the donor fluorescent label and detecting fluorescent emission from the fluorescence energy transfer pair.

In another preferred embodiment of the invention, a method for the detection of a target nucleic acid in sample is provided comprising the steps of amplifying the nucleic acid by polymerase chain reaction in the presence of two nucleic acid probes, whereby a probe is an oligomeric compound according to the invention, that hybridize to adjacent regions of the nucleic acid, one of said probes being labeled with an acceptor fluorescent label and the other probe labeled with donor fluorescent label of a fluorescence energy transfer pair such that upon hybridization of the two probes with the target nucleic acid, the donor and acceptor fluorescent labels are within 25 nucleotides of one another, said polymerase chain reaction comprising the steps of adding a thermostable polymerase, nucleotides and primers for the target nucleic acid to the sample and thermally cycling the sample between at least a denaturation temperature and an elongation temperature; exciting the sample with light at a wavelength absorbed by the donor label and monitoring temperature dependent fluorescence from the fluorescence energy transfer pair.

In another preferred embodiment of the invention, a method for determining the presence or the amount of a target nucleic acid in a sample comprising the steps of (a) providing a target nucleic acid from a sample to be analyzed, (b) synthesizing double stranded complementary DNA from the target nucleic acid, (c) amplifying the target nucleic acid in the presence of a compound according to the invention and nucleoside triphosphates whereby a labelled target nucleic acid is obtained (d) hybridizing the labelled target nucleic acid to an array of oligomeric compounds at a defined location, and (e) measuring the fluorescence intensities at each defined location whereby the presence or the amount of the target nucleic acid is determined.

This is the method which is used for the detection of target nucleic acids using the array format. Preferably, the method described in U.S. Pat. Nos. 5,545,522; 5,716,785; 5,891,636; 6,291,170 is used in steps b) and c) of the method according to the invention whereby double stranded cDNA is synthesized with a primer comprising the bacterial T7-Promoter and labeled RNA is transcribed in the presence of ribonucleoside triphosphates whereby labels are attached to some of the nucleoside triphosphates. The target nucleic acid in this case is preferably ribonucleic acid.

In another preferred embodiment a kit of parts is contemplated by the invention whereby the kit contains a template-dependent polymerase, preferably having 5' to 3' exonucleolytic activity, preferably the Taq Polymerase, a set of primers, nucleotides and a oligomeric compound according to the invention, preferably wherein $R^7$ is a label. Such kits known in the art further comprise plastics ware which can be used during the amplification procedure as e.g. microtiter plates in the 96 or 384 well format or just ordinary reaction tubes manufactured e.g. by Eppendorf, Hamburg, Germany and all other reagents for carrying out the method according to the invention.

In another preferred embodiment, a kit of parts is provided containing a compound according to the invention which is a triphosphate and can be enzymatically incorporated into nucleic acids. The kit further comprises nucleoside triphosphates and a polymerase, which may be e.g. ribonucleoside triphosphates and a RNA polymerase.

In another embodiment of the invention, the kit contains further reagents for isolating the nucleic acid. Therefore, the kit can additionally contain a material with an affinity to nucleic acids, preferably the material with an affinity to nucleic acids comprises a material with a silica surface. Preferably, the material with a silica surface is a glass. Most preferably, the material with an affinity to nucleic acids is a composition comprising magnetic glass particles as described in WO 96/41811 or WO 01/37291. The kit can further or additionally comprise a lysis buffer containing e.g. chaotropic agents, detergents or alcohols or mixtures thereof which allows the lysis of cells and separately a protease, e.g. proteinase K, for the digestions of unwanted proteins. These components of the kit according to the invention may be provided separately in tubes or storage containers. Depending on the nature of the components, these may be even provided in a single tube or storage container. The kit may further or additionally comprise a washing solution which is suitable for the washing step of the magnetic glass particles when DNA or RNA is bound thereto. This washing solution may contain ethanol and/or chaotropic agents in a buffered solution or solutions with an acidic pH without ethanol and/or chaotropic agents as described above. Often the washing solution or other solutions are provided as stock solutions which have to be diluted before use. The kit may further or additionally comprise an eluent or elution buffer, i.e. a solution or a buffer (e.g. 10 mM Tris, 1 mM EDTA, pH 8.0) or pure water to elute the DNA or RNA bound to the magnetic glass particles. Further, additional reagents or buffered solutions may be present which can be used for the purification process of a nucleic acid, i.e. DNA or RNA.

The following examples, references and figures are provided to aid the understanding of the present invention, the true scope of which is set forth in the appended claims. It is understood that modifications can be made in the procedures set forth without departing from the spirit of the invention.

DESCRIPTION OF THE FIGURES

FIG. 4: Overview of the substances synthesized for the incorporation studies in example 1.3.1

EXAMPLES

1. Preparative Examples

Synthesis of a Phosphoramidite

N-Fmoc-N'-acrylyl-1,6-diaminohexane

Figure 1:
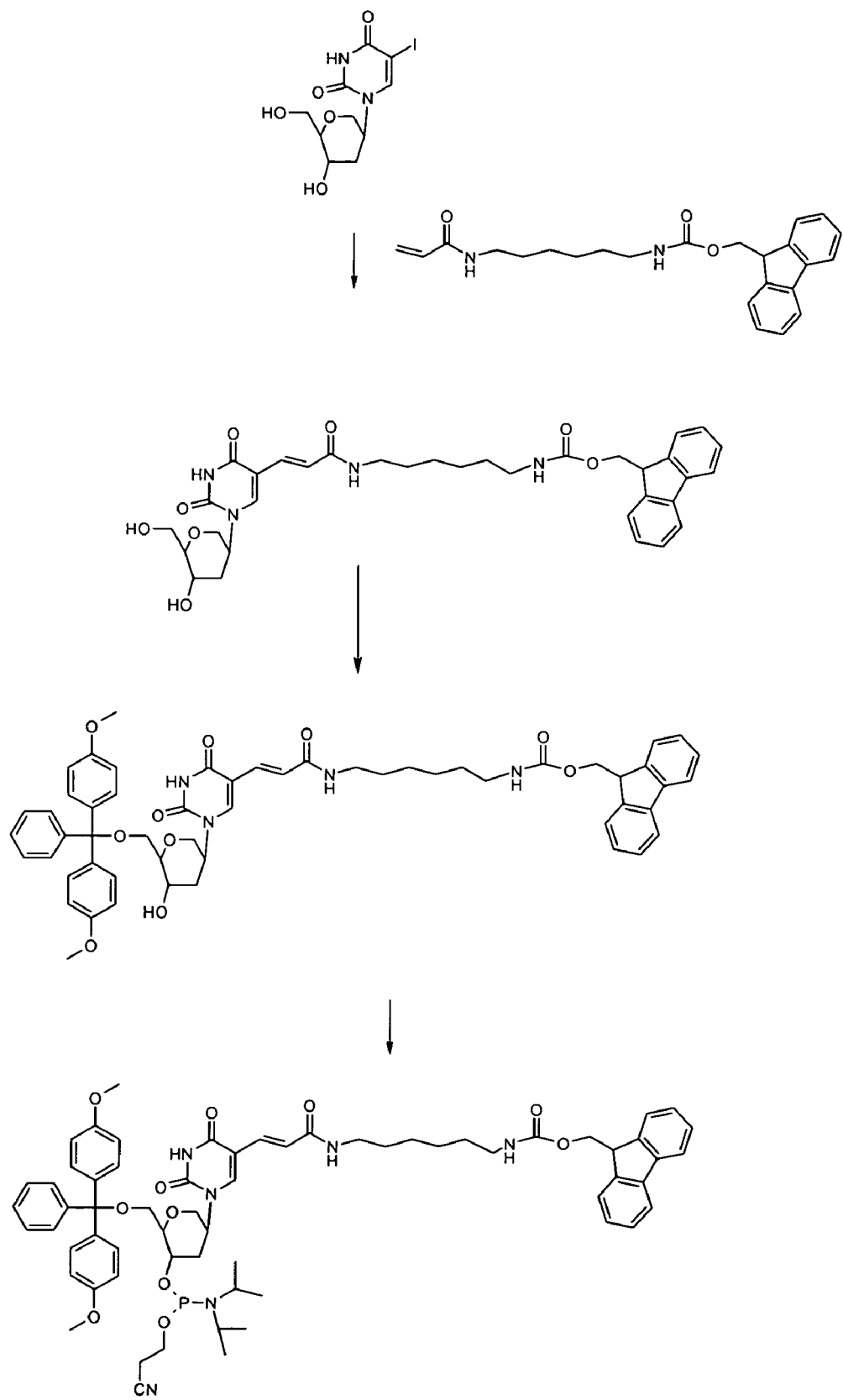
FIG. 1: Synthesis of a phosphoramidite derivative comprising uracil as the base, a linking moiety with a FMOC protected amino group as reactive group and a tetrahydropyran as the six-membered ring
Figure 2:
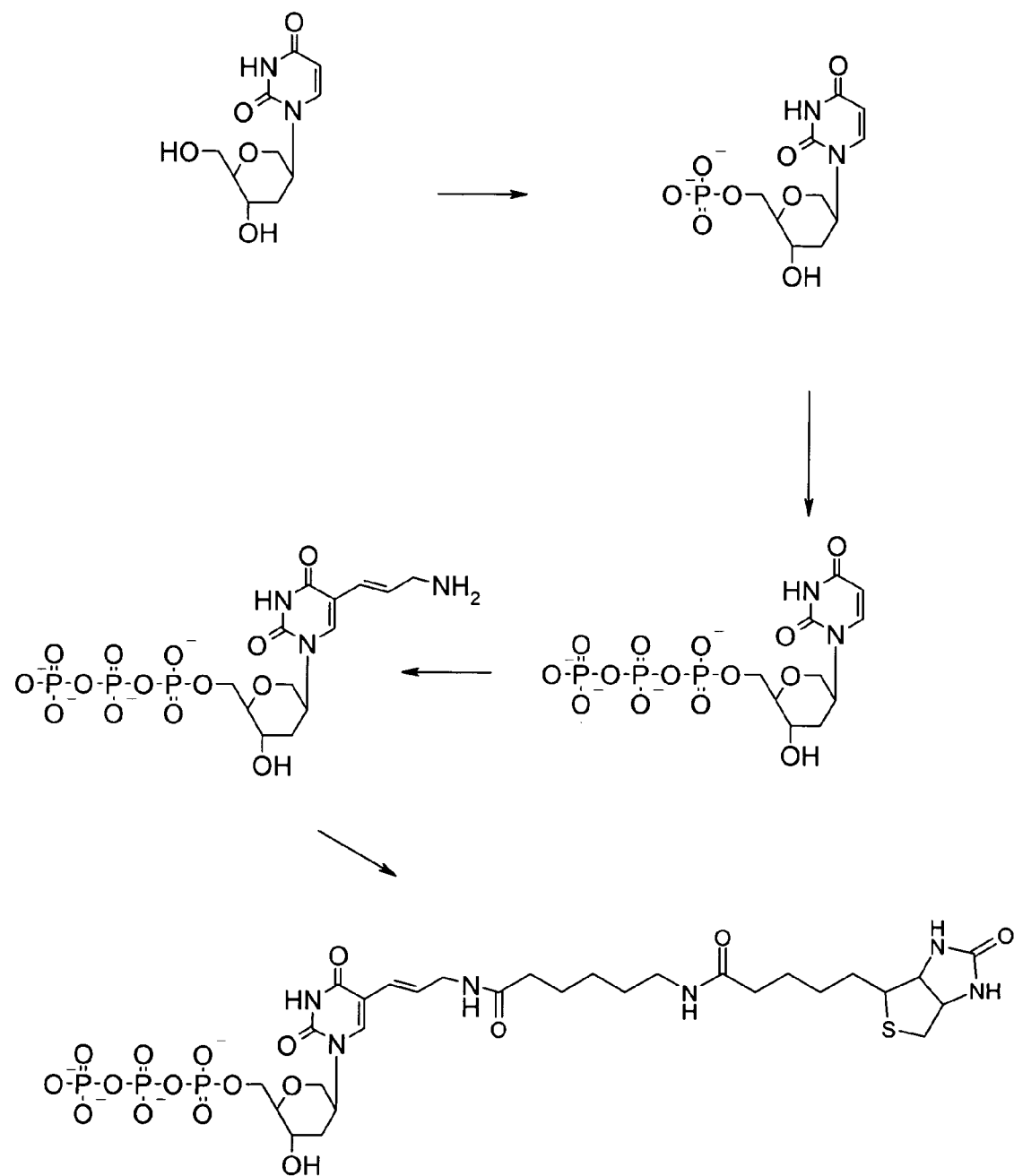
FIG. 2: Synthesis of 1,5-Anhydro-2-(5-(6-biotinamido-hexanoate amidoallyl-uracil-1yl)-2,3-dideoxy-D-arabino-hexitol 6 triphosphate FIG. 3: Synthesis of a triphosphate derivative comprising adenine as the base, biotin as the hapten, a linking moiety and a tetrahydropyran as the six-membered ring similar to the compound of FIG. 2
Figure 3:
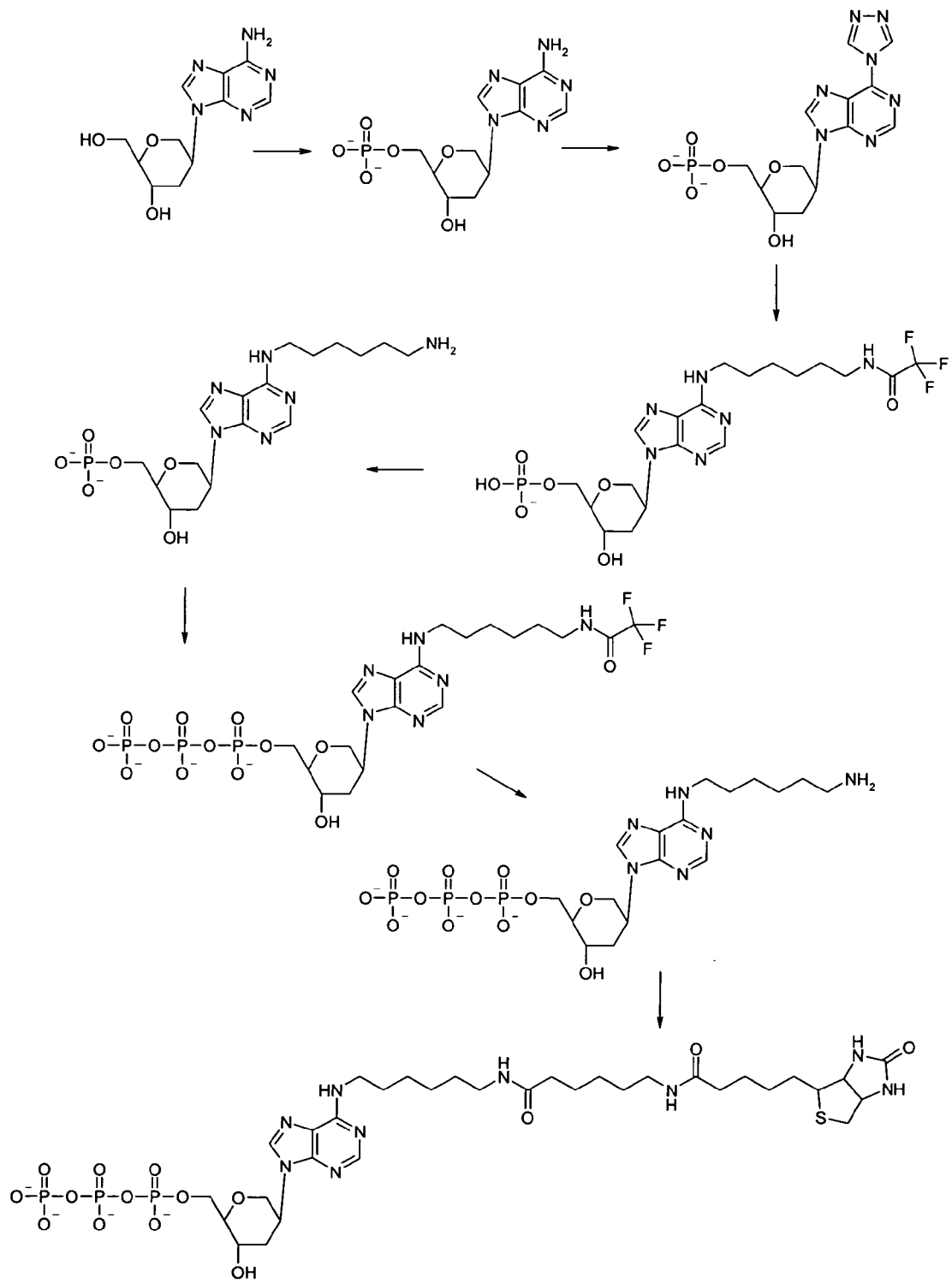

To 1.26 g (3 mmol) of Fmoc diaminohexane (Bachem Q 2045) in 90 ml of abs. chloroform were added 1.70 ml (12 mmol) of triethylamine. The mixture was cooled to 0° C. and 300 μl (3.6 mmol) of acrylic acid chloride were added dropwise. The mixture was allowed to warm to room temperature and was stirred overnight. The suspension was filtrated and the filtrate was evaporated at an rotary evaporator. The remainder was purified by column chromatography on silica gel with chloroform/methanol 4:1 as eluent (TLC control on silica gel chloroform/methanol 4:1: Rf=0.75). Fractions containing the product were collected and evaporated to dryness. Yield: 440 mg.

1,5-Anhydro-2-(5-(6-fluoren-9-ylmethoxycarbony-lamino-hexylcarbamoyl)-vinyl)-uracil-1yl)-2,3-dideoxy-D-arabino-hexitol 5.8 mg (0.023 mmol) of palladium acetate (Aldrich 20,586-9), 13 mg (0.05 mmol) of triphenylphosphine (Merck 808270) and 86 μl (0.61 mmol) of triethylamine were refluxed in 16 ml of abs. dioxane for 15 min. Then 392 mg (1 mmol) of N-Fmoc-N'-acrylyl-1,6-diaminohexaneand 180 mg (0.47 mmol) of 1,5-anhydro-2,3-dideoxy-2-(5-io-douracil-1-yl)-D-arabino-hexitol (Verheggen, I. et al J. Med. Chem. 38 (1995) 826-835) were added and the mixture was heated for 3 h at 80° C. The mixture was allowed to cool to room temperature and was filtrated. The filtrate was evaporated to dryness by using an rotary evaporator. The remainder was purified by column chromatography on silica gel with chloroform/methanol 5:1 as eluent. (TLC silica gel: chloroform/methanol 4:1: Rf=0.47)

The fractions containing the product were collected and evaporated to dryness using an rotary evaporator. Yield: 210 mg.

6-O-(4,4'-Dimethoxytrityl)-1,5-anhydro-2-(5-(6-fluoren-9-ylmethoxycarbonyl-amino-hexylcarbamoyl)-vinyl)-uracil-1yl)-2,3-dideoxy-D-arabino-hexitol 200 mg (0.32 mmol) of 1,5-Anhydro-2-(5-(6-fluoren-9-ylmethoxy-carbonylamino-hexylcarbamoyl)-vinyl)-uracil-1yl)-2,3-dideoxy-D-arabino-hexitol were coevaporated with 3×5 ml of abs. pyridine and then dissolved in 5 ml of abs. pyridine. Thereafter, 140 mg (0.39 mmol) of 4,4'-dimethoxytritylchloride in 5 ml of pyridine are added at room temperature within 15 min under stirring. The reaction mixture was stirred for another 2 h at room temperature. Then pyridine was evaporated and the residue was dissolved in 50 ml of ethyl acetate and washed twice with 50 ml of 0.1 M sodium phosphate buffer pH 7.5. Organic layer was separated, dried over sodium sulfate, filtered and evaporated to dryness. The residue was purified by flash-chromatography over silica gel (n-hexane/ethyl acetate/1% triethylamine gradient). Product fractions were combined, evaporated and dried at high vacuum. Yield: 235 mg.

6-O-(4,4'-Dimethoxytrityl)-1,5-anhydro-2-(5-(6-fluoren-9-ylmethoxycarbonyl-amino-hexylcarbamoyl)-vinyl)-uracil-1yl)-2,3-dideoxy-D-arabino-hexitol-4-O-[N,N-diisopropyl-(2-cyanoethyl)]-phosphoramidite 200 mg (0.21 mmol) of 6-O-(4,4'-Dimethoxytrityl)-1,5-anhydro-2-(5-(6-fluoren-9-ylmethoxy-carbonylamino-hexylcarbamoyl)-vinyl)-uracil-1yl)-2,3-dideoxy-D-arabino-hexitol were dissolved in 5 ml of dichloromethane under Ar-atmosphere. Thereafter 68 µl (0.38 mmol) of N-ethyldiisopropylamine, and within 15 min 72 mg (0.28 mmol) of chloro-2-cyanoethyoxy-diisopropylamino-phosphane in 5 ml of dichloromethane were added. The reaction mixture was stirred for 1 h at room temperature. Then 10 ml of dichloromethane were added. Reaction mixture was washed twice with 20 ml of 0.1 M sodium phosphate buffer pH 7.5. Organic layer was separated, dried over sodium sulfate, filtered and evaporated to dryness. The residue was purified by flash-chromatography over silica gel (n-hexane/acetone gradient). Product fractions were combined, evaporated and dried at high vacuum. Yield: 170 mg.

2. Preparative Example

Synthesis of Triphosphate 1,5-Anhydro-2-(adenin-9-yl)-2,3-dideoxy-D-arabino-hexitol 6 monophosphate dilithium salt 127 mg (0.48 mmol) of 1,5-Anhydro-2-(adenin-9-yl)-2,3-dideoxy-D-arabino-hexitol (Verheggen, I., et al., J. Med Chem. 36 (1993) 2033-2040) were dissolved in 12 ml Triethylphosphate and 260 µl Diisopropyl ethyl amine were added. The flask was cooled in an ice bath to 0-4° C. 36 µl Phosphoroxychloride were added. After stirring for 10 min at 0-4° Triethylamin/acetic acid buffer 0.1M pH 8.5 was added. The solvents were evaporated at 0.1 mbar at 40° C. using a rotary evaporator. The residue was dissolved in 20 ml water and purified by ion exchange on DEAE Sephadex A 25 Cl: Buffer A water, Buffer B 0.5 M LiCl, gradient in 60 min to 100% B monitoring by UV/VIS detector at 260 nm. The corresponding fractions were collected and evaporated at reduced pressure to a volume of 1–3 ml. The product solution was added to a 200 ml of a 2:1 mixture of Acetone/Ethanol. The suspension was centrifuged, the resulting pellet was washed 3 times with acetone to remove LiCl and then dried in high vacuum. yield 120 mg 1,5 Anhydro-2-(6-(1,2,4-triazol-4-yl)-purin-9-yl)-2,3-dideoxy-D-arabino-hexitol-6-monophosphate (Method described in Miles, W. M., et al., J. Am. Chem. Soc. 117 (1995) 5951-5957)

5 ml dried pyridine was added to 120 mg (0.34 mmol) of 1,5-Anhydro-2-(adenin-9-yl)-2,3-dideoxy-D-arabino-hexitol 6 monophosphate dilithiumsalt and 250 mg (1.2 mmol) 1,2-bis[(dimethylamino)methylene)]hydrazine and the mixture was evaporated.

2 ml Pyridine and 173 µl (1.36 mmol) mmol) Trimethylsilylchloride were added, the mixture was heated at 100° C. for 24 h. The solvent were evaporated in vacuum the residue was dissolved in water and purified by ion exchange chromatography on DEAE Sephadex A 25 Cl: Buffer A water, Buffer B 0.5 M LiCl, gradient in 60 min to 100% B monitoring by UV/VIS detector at 260 nm. The corresponding fractions were collected and evaporated to dryness at reduced pressure. The remainder was directly used for the next synthetic step without removing excess lithium chloride N6-(6-aminohexyl)-anhydro-2-(adenin-9-yl)-2,3-dideoxy-D arabino-hexitol-6-monophosphate triethylammonium salt The remainder of step II(1,5 Anhydro-2-(6-(1,2,4-triazol-4-yl)-purin-9-yl)-2,3-dideoxy-D-arabino-hexitol-6-monophosphate) was dissolved in 20 ml water filtrated and reacted with 1 ml diaminohexane for 15 h at 80° C. The mixture was evaporated at reduced pressure. The residue was dissolved in 5 ml 0.1 M Triethylammonium bicarbonate pH=8 and purified by ion exchange chromatography on DEAE Sephadex A 25 using a gradient form 0.1 m to 0.3 M Triethylammonium bicarbonate monitoring at 260 nm. Appropriate fractions (color development with Ninhydrin on TLC) were collected and evaporated under vacuum. The residue was diluted in water and evaporated again under vacuum. This process was repeated for three times. Yield 80 mg N6-(6-trifluoracetaminohexyl)-anhydro-2-(adenin-9-yl)-2,3-dideoxy-D arabino-hexitol-6-monophosphate 80 mg (0.12 mmol) N6-(6-aminohexyl)-anhydro-2-(adenin-9-yl)-2,3-dideoxy-D arabino-hexitol-6-monophosphate bis triethylammoniumsalt was dissolved in 10 ml of water 10 ml S-ethyltrifluorothiooacetate was added and the pH was adjusted to 10 with 5 M Lithiumhydroxide. The mixture was stirred for 4 h at room temperature. The mixture was diluted with 25 ml 0.1 M Triethylammonium bicarbonate pH=8 The solution was loaded on to a DEAE Sephadex Column and eluted with a gradient from 0.1-0.4 M Trieethylammoniumbicarbonate pH8 monitoring at 260 nm. The fractions containing the trifluoracetylated product were collected and evaporated under vacuum. Excess Triethylammoniumbicarbonate was removed by several coevaporations with water. Yield 82 mg

N6-(6-trifluoracetaminohexyl)-anhydro-2-(adenin-9-yl)-2,3-dideoxy-D arabino-hexitol-6-triphosphate 82 mg (0.11 mmol) N6-(6-trifluoracetaminohexyl)-anhydro-2-(adenin-9-yl)-2,3-dideoxy-D arabino-hexitol-6-monophosphate bis triethylammoniumsalt was dissolved in 3 ml dry DMF 89 mg(0.55 mmol) Carbonyldiimidazol were added the mixture was stirred for 2 h at RT. 0.5 ml Methanol were added and the mixture stirred for 20 min at RT. Methanol was removed by evaporation under reduced pressure. Then 0.7 ml of a 0.8 M solution of bis tributylammonium pyrophosphate in DMF (0.55 mmol)was added The mixture was stirred overnight at roomtemp. The solvents were evaporated at 0.1 mbar at 40° C. by using a rotary evaporator. The residue was dissolved in 5 ml 0.1 M Triethylammoniumbicarbonate pH=8 The solution was loaded on to a DEAE Sephadex Column and eluated with a gradient from 0.1-1 M Trieethylammoniumbicarbonate pH8 monitoring at 260 nm. The fractions containing the triphosphate were collected and evaporated under vacuum. Excess triethylammoniumbicarbonate was removed by several coevaporations with water. Yield 69 mg

N6-(6-aminohexyl)-anhydro-2-(adenin-9-yl)-2,3-dideoxy-D arabino-hexitol-6-triphosphate 69 mg (0.06 mmol) N6-(6-trifluoracetaminohexyl)-anhydro-2-(adenin-9-yl)-2,3-dideoxy-D arabino-hexitol-6-triphosphate was dissolved in 4 ml water was added and the pH adjusted to 11.5 with 6M NaOH The mixture was stirred for 4 h at room temperature. The pH was then adjusted to pH 8 with 2M HCl and 10 ml of 0.1 M Triethylammoniumbicarbonate pH=8 were added. The solution was loaded on to a DEAE Sephadex Column and eluated with a gradient from 0.1-1.0 M Trieethylammoniumbicarbonate pH8 monitoring at 260 nm. The fractions containing the triphosphate were collected and evaporated under vacuum. The presence of the aminogroup was verified by ninhydrine reaction Excess triethylammonium-bicarbonate was removed by several coevaporations with water. Yield 40 mg

N6-(6-(6-biotinamido-hexanoate)amidohexyl)-anhydro-9H (adenin-9-yl)-2,3-dideoxy-D arabino-hexitol-6-triphosphate 40 mg (0.03 mmol) N6-(6-aminohexyl)-anhydro-2-(adenin-9-yl)-2,3-dideoxy-D arabino-hexitol-6-triphosphate tetra triethylammoniumsalt was dissolved in 250 µl 0.1 M sodium borate buffer pH 8.5. A solution of 25 mg (0.055 mmol) biotin hexancarbonsäure NHS ester (Sigma ordering number B2643) in 800 µl amine free DMF was added. The mixture was stirred overnight at room temperature. The solvent was evaporated under vacuum. The remainder was dissolved in 5 ml 0.1 M triethylammoniumbicarbonate pH=8 The solution was loaded on to a DEAE Sephadex column and eluted with a gradient from 0.2-1.2 M Trieethylammoniumbicarbonate pH 8 monitoring at 260 nm. The fractions containing the biotinylated triphosphate were collected and evaporated under vacuum. Excess triethylammoniumbicarbonate was removed by several coevaporations with water. Yield 15 mg NMR (Bruker DPX 300, Solvent D$_2$O) $^1$H [ppm]: 1.10-1.85 (m) [22H], 2.18 (m) [4 H], 2.45 (d broad) [1H], 2.65(d) [1H], 2.85 (dd) [1H], 3.08 (m) [4H], 3.56 (s,broad) [2H], 3.61 (m) [2H], 3.79 (m) [1H], 4.08 (d) [1H], 4.28 (m) [4H], 4.50 (dd) [1H], 8.20 (s) [1H], 8.42 (s) [1H], $^{31}$P [ppm]: −21.77 (t); 10.08 (d); 9.50 (d)

N6-(6-(6-biotinamido-hexanoate)amidohexyl)-9-[1R,3S,4R)-3-hydroxy-4->-(tetrahydroxy-[1]triphosphoryl oxymethyl)cyclohexenyl]adenine tetratriethylammonium salt This compound was synthesized from 9-[1R,3S,4R)-3-Hydroxy-4-hydroxymethylcyclohexenyl]adenine (Wang J., Herdewijn P., J. Org. Chem. 64 (1999) 7820-7827.) by using the same synthesis pathway as described above.

NMR (Bruker DPX 300, Solvent D$_2$O) $^1$H [ppm]: 1.22 (t) [36H], 1.30-1.82 (m) [18H], 2.18 (m) [6 H], 2.51 (s, broad) [1H], 2.68 (d) [1H], 2.86 (dd) [1H], 3.28 (q) [24H], 3.56 (s,broad) [2H], 3.90 (q) [1H], 3.79 (m) [1H], 4.18 (m) [2H], 4.28 (m) [1H], 4.50 (dd) [1H], 5.98 (dt) [1H], 6.21 (d) (1H), 8.13 (s) [1H], 8.21 (s) [1H], $^{31}$P [ppm]: −22.04 (t); −9.72 (d); 9.53 (d)

1,5-Anhydro-2-(uracil-1yl)-2,3-dideoxy-D-arabino-hexitol 6 triphosphate 200 mg (0.82 mmol) 1,5-Anhydro-2-(uracil-1yl)-2,3-dideoxy-D-arabino-hexitol (Verheggen, I., et al., J. Med. Chem. 38 (1995) 826-835) was converted to 150 mg (0.44 mmol) monophosphate according to the procedure described above. The monophosphate was converted to the triphosphate according to the procedure described in Moffat, J. G., Khorana. H. G. J. Am. Chem. Soc. 1961, 83, 649-658. Therefore 150 mg (0.44 mmol) of 1,5-Anhydro-2-(uracil-1yl)-2,3-dideoxy-D-arabino-hexitol 6 monophosphate dilithium salt was converted in the free acid by passing through a Dowex H$^+$ form 50×8-100 column) It was eluated with water and the UV absorbing fractions were collected and concentrated to 2 ml. 2ml of tert butyl alcohol was added and the mixture was transferred in a two neck flask fitted with a reflux condenser and a rubber septum. 0.3 ml (3 mmol) morpholine were added using a syringe needle. The mixture was heated to reflux and a solution of 0.6 mg (2.9 mmol) dicyclohexylcarbodiimide in 3 ml tert butyl alcohol was added dropwise over a period of 2 h. The mixture was refluxed for 15 h. The mixture was cooled to room temperature and filtrated. The filtrate was concentrated to 2 ml and the concentrate was extracted three times with diethyl ether. The aqueous layer was evaporated to dryness in vacuum. The residue was dissolved in 5 ml DMF and added to a solution of 2.8 ml of a 0.8 M solution of bis tri-n-butylammonium pyrophosphate in DMF (2.2 mmol). The mixture was stirred overnight under Argon at room temperature. The solvents were evaporated at reduced pressure at 40° C. by using a rotary evaporator. The residue was dissolved in 5 ml water. The solution was loaded on to a DEAE The fractions containing the triphosphate were collected and concentrated to 5 ml under vacuum Sephadex column and eluated with a gradient from 0.1-1.2 M Lithiumchloride monitoring at 260 nm. The product solution was added to a 400 ml of a 2:1 mixture of Aceton/Ethanol. The suspension was centrifuged, the resulting pellet was washed 3 times with acetone to remove LiCl and than dried in high vacuum. yield 100 mg

1,5-Anhydro-2-(5-aminoallyl-uracil-1yl)-2,3-dideoxy-D-arabino-hexitol 6 triphosphate 100 mg (0.19 mmol)of 1,5-Anhydro-2-(uracil-1yl)-2,3-dideoxy-D-arabino-hexitol 6 triphosphate and 106 mg (0.33 mmol) mercury II acetate were dissolved in 5 ml 0.1 M sodium acetate buffer pH5 The mixture was stirred for 4 h at 50° C. after cooling to room temperature the mixture was diluted with 40 ml water. A freshly prepared allylamine acetate solution. (0.77 ml (13 mmol) were neutralized with 4M acetic acid) and 150 mg (1.5 mmol) dipotassium tetrachloropalladinate were added and the mixture was stirred for 24 h at room temperature. The reaction mixture was filtered through a 0.45 µm membrane filter and the filtrate was applied on a DEAE-Sephadex column and it was eluated with a gradient from 0.1-1 M Trieethylammoniumbicarbonate pH8 monitoring at 260 nm. The major UV peak was collected (Ninhydrine reaction positive) and further purified by reversed phase chromatography with a gradient from buffer 100% A: 0.1M triethylammonium acetate pH 8.0 to 100% buffer B: 0.1 M triethylammonium acetate/Acetonitril 1:1 monitoring at 260 nm on a RP 18 Hypersil column) The fractions containing the aminoallyl triphosphate were collected and evaporated under vacuum. The presence of the aminogroup was verified by ninhydrine reaction Excess triethylammonium-acetate was removed by several coevaporations with water. Yield 80 mg 1,5-Anhydro-2-(5-(6-biotinamido-hexanoate amidoallyl-uracil-1yl)-2,3-dideoxy-D-arabino-hexitol 6 triphosphate 80 mg (0.08 mmol) were labeled with biotin hexancarbonsäure NHS ester (Sigma ordering number B2643) in borate buffer/DMF according to the procedure described above. Yield: 10 mg NMR (Bruker DPX 300, Solvent D2O) 1H [ppm]: 1.28 (t) [36H], 1.66 (m) [10H], 1.92 (m) [1 H], 2.19 (dd) [1H], 2.31 (dd) [1H], 2.72 (d) [1H], 2.95 (dd) [1H], 3.18 (q) [24H], 3.28 (m,) [2H], 3.59 (d,broad) [1H], 3.95 (m) [2H], 4.21 (m) [2H], 4.40 (dd [1H], 4.56 (dd) [1H], 4.70 (s) [1H], 6.20 (d) [1H], 6.38 (dt) (1H), 8.21 (s) [1H] 31P [ppm]: −22.04 (t); −9.83 (d); 9.61 (d)

3. Functional Example

Incorporation Studies

Figure 5A:
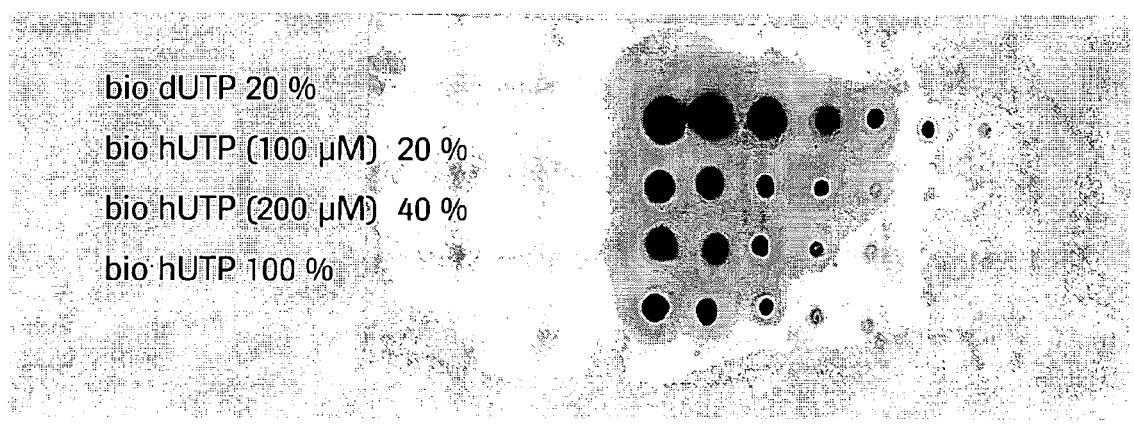
FIG. 5: Dot blot of incorporation studies (see example 1.3.1)
Figure 5B:
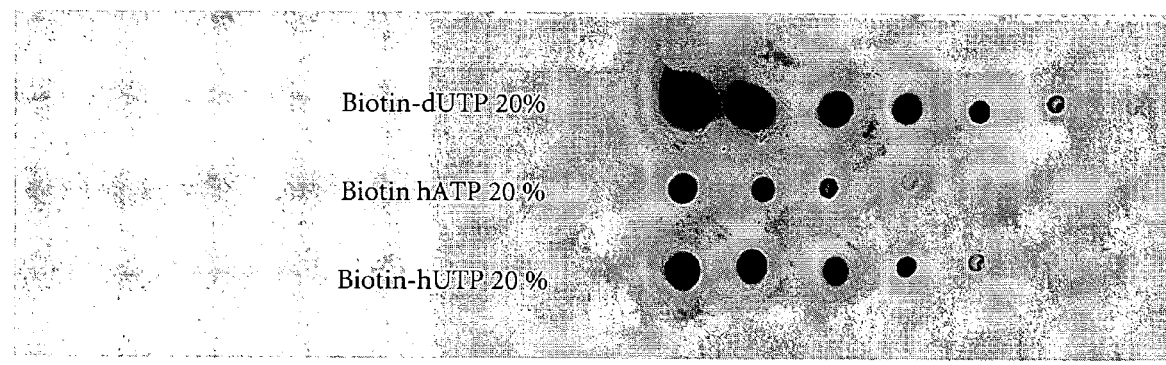
Figure 5C:
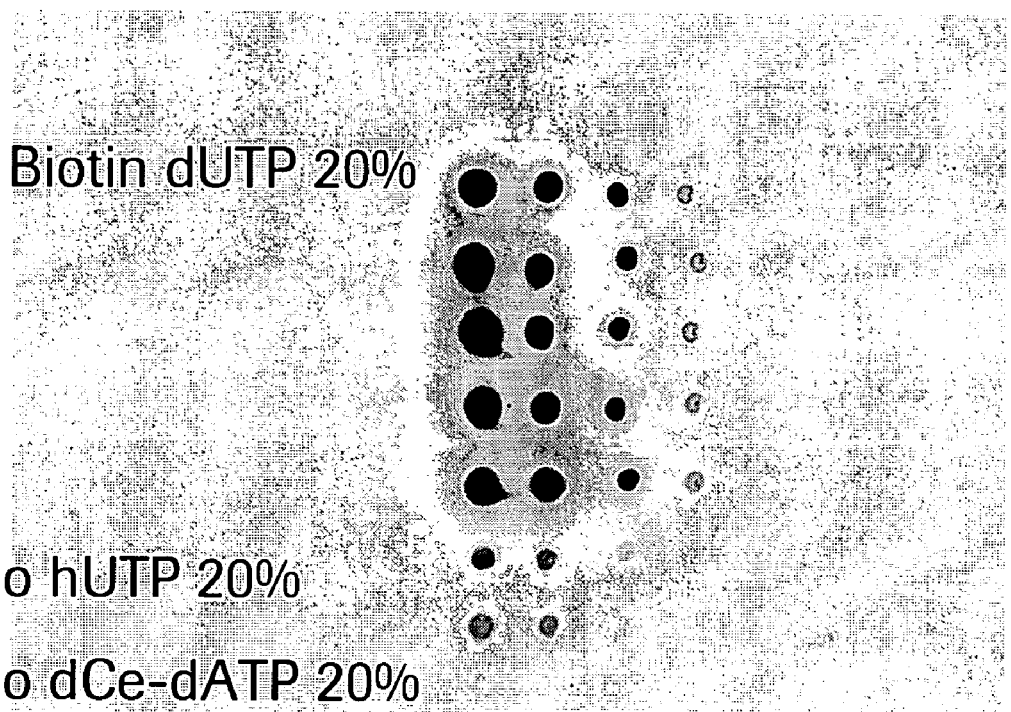

Incorporation rates of biotinylated hUTP, hATP and CeATP (see FIG. 4) which are considered to be 2' deoxy-NTP analogs were compared with the standard biotin-16-dUTP via a dot blot dilution series of cDNAs labeled using AMV reverse transcriptase. Firstly, we investigated the influence of different ratios biotin hUTP:dUTP based on a dot blot dilution series (detection with SA-AP/CPD*). We found that a 1:4 ratio (=20%) is sufficient for labeling. Using this ratio different analogs were compared with biotin dUTP. Incorporation efficiency increases in the row biotin hATP<biotin hUTP=biotin dCeATP<biotin dUTP (see FIG. 5a-c)

Figure 6:
FIG. 6: Dot blot of incorporation studies (see example 1.3.1)
Figure 6:
Figure 6:
Figure 6:
Figure 6:
Figure 6:
Figure 6:
Figure 6:
Figure 6:
Figure 6:
Figure 6:
Figure 6:

Another analog we studied was aUTP which has an additional hydroxyl group and therefore is similar to a ribonucleoside. We investigated incorporation of biotin aUTP with different RNA polymerases. T7 RNA polymerase is the best choice for incorporation of biotin aUTP. However, incorporation yield is by a factor of approx. 25 times lower compared to biotin UTP (see FIG. 6).

Microarray-Based Expression Profiling Experiment

The performance of Bio-h-dUTP was tested in a microarray based expression-profiling experiment. This application enables researcher to monitor mRNA levels of many genes in parallel. For this purpose oligonucleotides were covalently attached to a solid surface (i.e. glass slide) in an ordered fashion. In the next step this array of oligonucleotides is hybridized with a pool of target molecules derived from a defined sample (i.e. tissue, cell line, etc.). For target synthesis total RNA has to be isolated from the sample. Afterwards mRNA is primed with an oligo dT primer followed by an enzymatically cDNA synthesis using reverse transcriptase. During this step Biotin labeled nucleotides are inserted into the cDNA strand. For hybridization cDNA is purified and applied onto the array. Incubation was carried out over-night followed by a stringent wash procedure. After washing of the array incubation with a fluorophore labeled streptavidine conjugate was performed. For signal detection, glass slides were scanned with a convocal laser scan microscope in order to quantify the amount of hybridized target molecules. By utilizing computational analysis signal intensities were correlated to the distinct oligonucleotide representing a specific gene.

Experimental Procedure in Detail

Glass arrays were ordered containing oligonucleotides specific for distinct rat genes (rat oligo test set) in triplicate (MWG-Biotech AG, Ebersberg, Germany). RNA isolation was performed by utilizing the RNeasy Kit (QIAGEN, Hilden, Germany) according to the kit manual. One hundred micro gram of total mouse RNA derived from liver isolated from a liver tissue sample served as template for target preparation using a cDNA synthesis kit (Roche, Mannheim, Germany), including incorporation of labeled Bio-h-dUTP. Labeling procedure: 100 µg of total RNA was incubated 10 minutes at 70° C. in 18 µl $H_2O$ with 2 µg of a oligo dT 24 mer and chilled on ice. Reaction mix containing: 5 µl RT-buffer, 4 µl DTT, 4 µl dNTP (5 mM A,G,C and 3 mM T), 0.4 µl Bio-h-dUTP, 1.8 µl AMV reverse Transcriptase, 0.2 µl RNAsin, 3.5 µl $H_2O$ was added and incubated for 1 hour at 42° C. The labeling reaction was terminated by adding 10 µl of 1N NaOH followed by a 10 minute incubation at 65° C. Solution was neutralized with 10 µl of 1N HCl and 22 µl of 1M TrisHCl (pH=7.5). The purification of the labeled target was performed with HighPure spin columns (Roche, Mannheim, Germany) according to instruction manual.

Hybridization of the arrays was performed for 16 hours in a humidity chamber according to the instructions of the glass array manufacturer.

After hybridization the array was washed three times for 5 minutes at 30° C. in 2×SSC+1% SDS, 1×SSC and 0.5× SSC respectively.

Antibody detection was performed by preblocking for 30 minutes in 2×SSC and 1% caseine as well as incubation for 10 minutes with streptavidine-Cy3 (1 µg/ml) in 2×SSC+1% caseine. Final washing was performed two times for 5 minutes in 2×SSC+0.2% SDS as well as one time for 5 minutes in 2×SSC.

For signal detection the array was scanned with a confocal laser scanner (Axon, Union City, USA) with a PMT setting as well as a gain of 80. Image analysis was performed with Imagene software (BioDiscovery, Marina del Rey, USA).

Results

Figure 7:
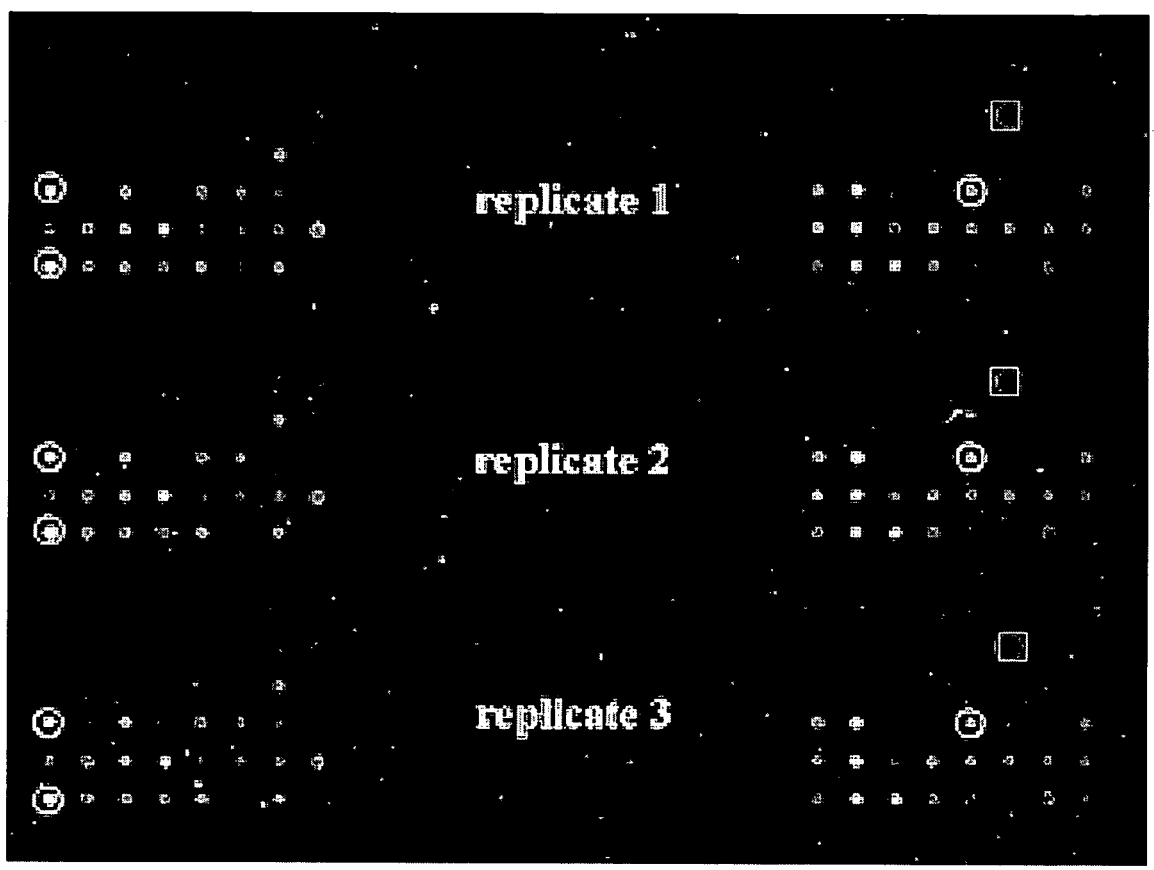
FIG. 7: Image of a glass array after hybridization with Bio-h-dUTP labeled cDNA derived from rat tissue (Squares: negative control spots; Circles: probes for neuronal cannabinoid receptor expressed in liver, kidney; Alpha-1 microglobulin/bikunin ambp expressed in liver and Gapd expressed in all tissues)

As expected control spots containing probe sequences matching with none of the target sequences revealed no signal and therefore ensure specificity within the hybridization procedure. Also spots corresponding to genes not known to be expressed in liver revealed low or no signal. On the other hand genes expressed in wide range of tissues as well as genes specific for liver were clearly detected demonstrating the good performance of Bio-h-dUTP in this approach (see FIG. 7).

LIST OF REFERENCES

Abramson, R. D., and Myers, T. W., Current Opinion in Biotechnology 4 (1993) 41-47
Allart, B., et al., Chem. Eur. J. 8 (1999) 2424-2431
Allart, B., et al., Tetrahedron 55 (1999) 6527-6546
Andersen, M. W., et al., Pergamon, Tetrahedron Lett. 37 (1996) 8147-8150
Arango, J. H., Nucleosides & Nucleotides 12 (1993) 773-784
Atkins, D., et al., Pharmazie 55 (2000) 615-617
Barany, F., PCR Methods and Appl. 1 (1991) 5-16
Barany, F., Proc. Natl. Acad. Sci. USA 88 (1991)189-193
Beaucage, S. L., and Caruthers, M. H., et al., Tetrahedron Letters 22 (1981) 1859-1862
Boudou, V., et al., Nucleic Acids Research 27 (1999) 1450-1456
Brown, E. L., et al., Methods in Enzymology 68 (1979) 109-151
Brown, S. G., et al., Drug Development Research 49 (2000) 253-259
Chou, Q., et al., Nucl. Acids. Res. 20 (1992) 1717-1723
De Bouvere, B., et al., Liebigs Ann./Recueil (1997) 1453-1461
De Winter, H., et al., J. Am. Chem. Soc. 120 (1998) 5381-5394
DE 3943522
EP 0468352
EP 0476014
EP 0135587
EP 0313219
EP 0439182
Froeyen, M., et al., Helvetica Chimica Acta 83 (2000) 2153-2182
Gait, M. J., Oligonucleotide Synthesis, ed. (1984)
Garegg et al., Chem. Scr. 25 (1985) 280
Giegrich et al., Nucleosides & Nucleotides 17 (1998) 1987
Guatelli, J. C., et al., Proc. Natl. Acad. Sci. USA 87 (1990) 1874-1878
Hames, B. D, and Higgins, S. J., Nucleic Acid Hybridization, eds. (1984)
Hendrix, C., et al., Chem. Eur. J. 3 (1997) 110-120
Hendrix, C., et al., Chem. Eur. J. 3 (1997) 1513-1520
Herdewijn, P., et al., Nucl. Acids Symp. Series 31 (1994) 161-162
Hoheisel, J. D., TIBTECH 15 (1997) 465-469
Hossain, N., et al., J. Org. Chem. 63 (1998) 1574-1582
JP 60016982
Jung, K.-E., Bioorg. Med. Chem. Lett. 9 (1999) 3407-3410
Katagiri, N., et al., Nucleosides & Nucleotides 15 (1996) 631-647
Konkel, M. J., and Vince, R., Nucleosides & Nucleotides 14 (1995) 2061-2077
Konkel, M. J., and Vince, R., Tetrahedron 52 (1996) 799-808
Kozlov, I. A., et al., Chemistry 6 (2000) 151-155
Kozlov, I. A., et al., J. Am. Chem. Soc. 121 (1999) 2653-2656
Kozlov, I. A., et al., J. Am. Chem. Soc. 121 (1999) 1108-1109
Kozlov, I. A., et al., J. Am. Chem. Soc. 121 (1999) 5856-5859
Kwoh, D. Y., et al., Proc. Natl. Acad. Sci. USA 86 (1989) 1173-1177
Lescrinier, E., et al., Chem. Biol. 7 (2000) 719-731
Lescrinier, E., et al., Helvetica Chimica Acta 83 (2000) 1291-1310
Luyten, I., and Herdewijn, P., Tetrahedron 52 (1996) 9249-9262
Maurinsh, Y., et al., Chem. Eur. J. 5 (1999) 2139-2150
Maurinsh, Y., et al., J. Org. Chem. 62 (1997) 2861-2871
Miles, W. M., et al., J. Am. Chem. Soc. 117 (1995) 5951-5957
Narang, S. A., et al., Methods in Enzymology 68 (1979) 90-98
Ostrowski, T., et al., J. Med. Chem. 41 (1998) 4343-4353
Pérez-Pérez, M. J., et al., J. Org. Chem. 60 (1995) 1531-1537
Pérez-Pérez, M.-J., et al., Bioorg. & Med. Chem. Lett. 6 (1996) 1457-1460
Pochet, S., et al., Nucleosides & Nucleotides 18 (1999) 1015-1017
Pravdic, N., et al., Croatica Chemica Acta 45 (1973) 343-356
Ramesh, K., et al., J. Org. Chem. 57 (1992) 5861-5868
Rosenquist, A., et al., J. Org. Chem. 61 (1996) 6282-6288
Sambrook et al., Molecular Cloning: A Laboratory Manual, Cold Spring Harbor Laboratory, Cold Spring Harbor, N.Y., 1989
Sheng-Hui, S., et al., Bioorganic & Medicinal Chem. Lett. 7 (1997) 1639-1644
Uhlmann and Peyman, Chemical Reviews 90 (1990) 543
U.S. Pat. No. 5,002,867
U.S. Pat. No. 5,143,854
U.S. Pat. No. 5,202,231
U.S. Pat. No. 5,338,671
U.S. Pat. No. 5,411,876
U.S. Pat. No. 5,418,149
U.S. Pat. No. 6,022,963
U.S. Pat. No. 6,156,501
U.S. Pat. No. 4,458,066
U.S. Pat. No. 4,996,143
U.S. Pat. No. 5,130,238
U.S. Pat. No. 5,210,015
U.S. Pat. No. 5,314,893
U.S. Pat. No. 5,451,463
U.S. Pat. No. 5,487,972
U.S. Pat. No. 5,565,322
U.S. Pat. No. 5,804,375
U.S. Pat. No. 5,849,489
U.S. Pat. No. 6,103,476
U.S. Pat. No. 6,130,323
U.S. Pat. No. 6,162,603
U.S. Pat. No. 6,174,670
Van Aerschot, A., et al., Angew. Chem. Int. Ed. Engl. 34 (1995) 1338-1339
Van Aerschot, A., et al., Bioorganic & Medicinal Chemistry Letters (1993) 1013-1018
Vandermeeren, M., et al., Biochem. Pharm. 59 (2000) 655-663
Vastmans, K., et al., Biochem. 39 (2000) 12757-12765
Vastmans, K., et al., Collect. Symp. Series 2 (1999) 156-160
Verheggen, I., et al., J. Med. Chem. 36 (1993) 2033-2040
Verheggen, I., et al., J. Med. Chem. 38 (1995) 826-835
Verheggen, I., et al., Nucleosides & Nucleotides 15 (1996) 325-335

Verma, S., and Eckstein, F., Annu. Rev. Biochem. 67 (1998) 99-134
Wang, J., and Herdewijn, P., J. Org. Chem. 64 (1999) 7820-7827
Wang, J., et al., J. Am. Chem. Soc. 122 (2000) 8595-8602
Wang, J., et al., J. Med. Chem. 43 (2000) 736-745
Wang, J., et al. Nucleosides Nucleotides Nucleic Acids 20 (2001) 785-788
Whelen, A. C., and Persing, D. H., Annu. Rev. Microbiol. 50 (1996) 349-373
WO 01/02417
WO 02/072779
WO 89/10977
WO 89/11548
WO 90/15070
WO 92/10092
WO 93/17126
WO 97/27317
WO 98/25943
WO 99/09044
WO 99/15509
WO 01/37291
WO 02/12263
WO 90/01069
WO 92/08808
WO 93/25565
WO 96/41811
WO 9605213
WO 97/43451
Wu, D. Y., and Wallace, R. B., Genomics 4 (1989) 560-569

What is claimed is:

1. A compound comprising a structure of the formula

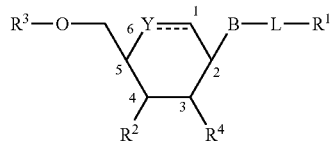

wherein L is a linking moiety;
B is a heterocyclic base;
$R^1$ is selected from the group consisting of a protecting group, a label, a solid phase, and —H;
$R^2$ is selected from the group consisting of —H and —$OR^6$;
$R^3$ is selected from the group consisting of a protecting group, a linking moiety covalently coupled to a solid phase, a phosphate, a phosphoramidite, an H-phosphonate, and a triphosphate;
$R^4$ is selected from the group consisting of —H, —OH, alkyl, halogen, —O—$R^5$, —S—$R^5$, $NR^5R^{5a}$, a label, and a linking moiety covalently coupled to a solid phase;
$R^5$ is selected from the group consisting of —H, a protecting group, a linking moiety covalently coupled to a solid phase, a phosphoramidite, and a H-phosphonate;
Y is selected from the group consisting of O, S, $NR^5$, $CR^{5a}R^{5b}$, and $CR^{5a}$, and the bond between the C-1 atom of the six-membered ring and Y is a single bond When Y is O, S, $NR^5$, or $CR^{5a}R^{5b}$ and a double bond when Y is $CR^{5a}$; and $R^5$ is selected from the group consisting of alkyl, alkenyl, alkinyl, aryl, acyl, a protecting group, and —H and $R^{5a}$ and $R^{5b}$ are selected front the group consisting of alkyl, alkenyl, alkinyl, aryl, acyl, and —H, with the proviso that when $R^1$, $R^3$, or $R^6$ is a solid phase, then the other two residues selected from the group consisting of $R^1$, $R^2$, and $R^6$ are not a solid phase.

2. The compound according to claim 1 wherein the linking moiety L comprises carbon, oxygen or nitrogen atoms and a reactive group.

3. The compound according to claim 1 wherein R1 is a label selected from the group consisting of a dye and a hapten.

4. The compound according to claim 3 wherein R1 is a dye selected from the group consisting of a fluorescein dye, a rhodamine dye, a cyanine dye, a coumarin dye, and an azo dye.

5. The compound according to claim 3 wherein the hapten is biotin.

6. A compound comprising a structure of the formula

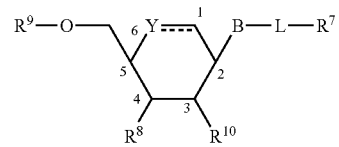

wherein
L is a linking moiety;
B is a heterocyclic base;
$R^1$ is selected from the group consisting of a protecting group, a label, a solid phase, and —H;
$R^2$ is selected from the group consisting of —H and —$OR^6$;
$R^3$ is selected from the group consisting of a protecting group, moiety covalently coupled to a solid phase, a phosphate, a phosphoramidite, an H-phosphonate, and a triphosphate;
$R^4$ is selected from the group consisting of —H, —OH, alkyl, halogen, —O—$R^5$, —S—$R^5$, $NR^5R^{5a}$, a label, and a linking moiety covalently coupled to a solid phase;
$R^5$ is selected from the group consisting of —H, a protecting group, a linking moiety covalently coupled to a solid phase, a phosphoramidite, and a H-phosphonate;
Y is $CR^{5a}$ wherein $R^{5a}$ is selected from the group consisting of alkyl, alkenyl, alkinyl, aryl, acyl, and —H, and the bond between the C-1 atom of the six-membered ring is a double bond; and
$R^5$ is selected from the group consisting of alkyl, alkenyl, alkinyl, aryl, acyl, a protecting group, and —H, and $R^{5a}$ and $R^{5b}$ are selected from the group consisting of alkyl, alkenyl, alkinyl, aryl, acyl, and —H.

7. The compound according to claim 1 wherein Y is selected from the group consisting of O, S, and $CR^{5a}R^{5b}$.

8. The compound according to claim 1 wherein $R^3$ is a triphosphate, $R^2$ is —$OR^6$ wherein $R^6$ is —H, and $R^4$ is —H or —OH.

9. A compound having the formula:

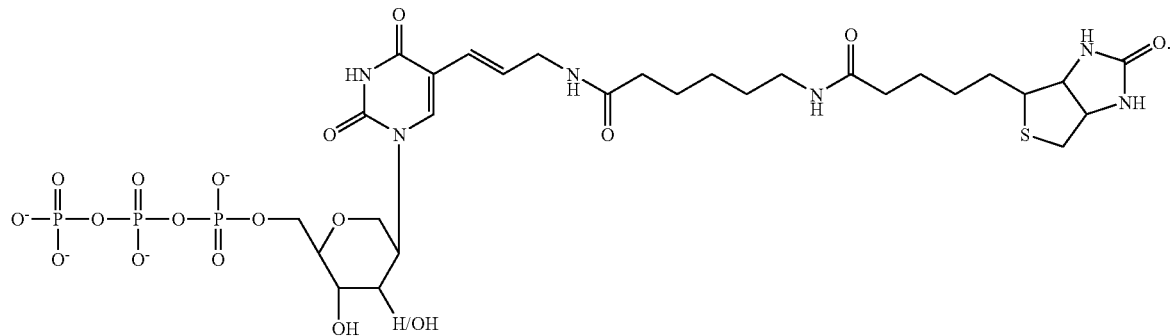

10. The compound according to claim 1 wherein $R^2$ is —$OR^6$ wherein $R^6$ is a phosphoramidite and $R^3$ is a protecting group or a solid phase covalently coupled to a linking moiety.

11. A kit of parts comprising a compound according to claim 8, nucleoside triphosphates, and a polymerase.

12. A kit of parts comprising a compound according to claim 9, nucleoside triphosphates, and a polymerase.

13. The compound according to claim 8 wherein B is a heterocyclic base selected from the group consisting of adenine, guanine, cytosine, thymine, uracil, and methylcytosine.

14. The compound according to claim 1 wherein $R^2$ is —$OR^6$ wherein $R^6$ is a phosphoramidite and $R^3$ is a protecting group or a solid phase.

15. The compound according to claim 14 wherein $R^4$ is —H or —OH.

16. The compound according to claim 15 wherein Y is selected from the group consisting of O, S, and $CR^{5a}R^{5b}$.

17. The compound according to claim 1 wherein B is a heterocyclic base selected form the group consisting of adenine, guanine, cytosine, thymine, uracil, and methylcytosine, Y is O, and $R^4$ is —H or —OH.

* * * * *